(12) United States Patent
Bodurka et al.

(10) Patent No.: US 11,804,125 B2
(45) Date of Patent: *Oct. 31, 2023

(54) HOSPITAL HEADWALL COMMUNICATION SYSTEM

(71) Applicant: Stryker Corporation, Kalamazoo, MI (US)

(72) Inventors: Alexander Josef Bodurka, Portage, MI (US); Jerald A. Trepanier, Augusta, MI (US); Krishna Sandeep Bhimavarapu, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/883,071

(22) Filed: Aug. 8, 2022

(65) Prior Publication Data

US 2022/0384033 A1 Dec. 1, 2022

Related U.S. Application Data

(63) Continuation of application No. 17/186,097, filed on Feb. 26, 2021, now Pat. No. 11,410,532, which is a
(Continued)

(51) Int. Cl.
*G08B 25/00* (2006.01)
*A61G 7/05* (2006.01)
*H04L 43/10* (2022.01)
*A61G 12/00* (2006.01)
*G16H 40/67* (2018.01)
(Continued)

(52) U.S. Cl.
CPC ............. *G08B 25/004* (2013.01); *A61G 7/05* (2013.01); *A61G 12/00* (2013.01); *G16H 40/20* (2018.01); *G16H 40/67* (2018.01); *H04L 43/10* (2013.01); *A61G 7/002* (2013.01); *A61G 7/018* (2013.01); *A61G 2205/60* (2013.01); *G16H 40/63* (2018.01)

(58) Field of Classification Search
None
See application file for complete search history.

(56) References Cited

U.S. PATENT DOCUMENTS

2016/0038361 A1\* 2/2016 Bhimavarapu .......... A61G 7/05
398/115

\* cited by examiner

*Primary Examiner* — Adolf Dsouza
(74) *Attorney, Agent, or Firm* — Warner Norcross + Judd LLP

(57) ABSTRACT

A patient support apparatus includes a first transceiver adapted to wirelessly communicate with a second transceiver of a headwall interface that is positioned off of the patient support apparatus. A communication link is automatically established between the first and second transceivers without requiring a user of the patient support apparatus to activate a designated control and without requiring the user to identify the headwall interface. The first transceiver includes a unique identifier assigned to the headwall interface in its messages to the headwall interface. The first transceiver may also automatically transmit a disconnect signal to the headwall interface indicating the termination of the communication link is not accidental. The disconnect signal is sent based on one or more of the following: (1) a brake being off, (2) an A/C power cord being unplugged; and/or (3) a signal strength between the transceivers decreasing.

20 Claims, 9 Drawing Sheets

Related U.S. Application Data continuation of application No. 16/893,797, filed on Jun. 5, 2020, now Pat. No. 10,950,117, which is a continuation of application No. 16/215,911, filed on Dec. 11, 2018, now Pat. No. 10,679,489.

(60) Provisional application No. 62/598,787, filed on Dec. 14, 2017.

(51) Int. Cl.
*G16H 40/20* (2018.01)
*A61G 7/018* (2006.01)
*G16H 40/63* (2018.01)
*A61G 7/002* (2006.01)

HOSPITAL HEADWALL COMMUNICATION SYSTEM

CROSS-REFERENCE TO RELATED APPLICATIONS

This application claims priority to U.S. patent application Ser. No. 17/186,097 filed Feb. 26, 2021, by inventors Alexander Bodurka et al. and entitled HOSPITAL HEADWALL COMMUNICATION SYSTEM, which in turn claims priority to U.S. patent application Ser. No. 16/893,797 filed Jun. 5, 2020, by inventors Alexander Bodurka et al. and entitled HOSPITAL HEADWALL COMMUNICATION SYSTEM, which in turn claims priority to U.S. patent application Ser. No. 16/215,911 filed Dec. 11, 2018, by inventors Alexander Bodurka et al. and entitled HOSPITAL HEADWALL COMMUNICATION SYSTEM, which in turn claims priority to U.S. provisional patent application Ser. No. 62/598,787 filed Dec. 14, 2017, by inventors Alexander Bodurka et al. and entitled HOSPITAL HEADWALL COMMUNICATION SYSTEM, the complete disclosures of all of which are incorporated herein by reference.

BACKGROUND

The present disclosure relates to medical facilities having headwalls with one or more connectors that enable communication between a patient support apparatus (e.g. a bed, stretcher, cot, recliner, wheelchair, etc.) and one or more devices that are coupled to a headwall communication interface (e.g. a nurse call system, entertainment controls, room controls, etc.).

Medical facilities, such as hospitals, typically include a headwall having one or more ports and/or other types of connectors into which the plugs of cables connected to medical devices can be inserted. For example, headwalls will typically include at least one port that interfaces with a nurse-call system and which is designed to accept a cable from a hospital bed, or from a hand-held pendant positioned on the bed. When the cable is plugged into this port, a patient positioned on the bed is able to press a button to summon a nurse and/or to communicate aurally with the nurse.

Existing headwall connectors also typically communicate with one or more environmental controls, such as one or more controls for in-room televisions, displays, and/or room lights. When the appropriate device and its associated cable are plugged into the headwall connector from a bed, pendant, or other device, a person is able to control the environmental control via the device (e.g. bed, pendant, or other device). Thus, for example, a patient positioned on a bed is able to control the volume of a television in the room via controls on the bed due to a cable being connected from the bed to the headwall. In some instances, a single cable is plugged into a single connector on the headwall and used for communicating both with the nurse call system of the medical facility, and for communicating with the one or more environmental controls. In such instances, the headwall connector is coupled to a room interface board that forwards the environmental control signals to the appropriate environmental control unit, and forwards the nurse call signals to the appropriate component of the nurse call system.

SUMMARY

A headwall system includes a headwall unit mounted to a fixed location within a healthcare facility room. The headwall unit wirelessly communicates with a patient support apparatus in that room in order to allow a patient on the patient support apparatus to communicate with a healthcare worker positioned remotely, such as at a nurses' station. Additional communication between the headwall unit and patient support apparatus may take place. The headwall unit and/or patient support apparatus provide automatic linking to each other, improved security and resilience to communication failure, reduced energy consumption, and automated adjustments between wired and wireless communication in response to manual steps taken by a caregiver. These and other features are described in more detail below.

According to one embodiment of the present disclosure, a patient support apparatus is provided that includes a support surface, a first transceiver, a second transceiver, and a controller. The support surface is adapted to support a patient thereon. The first and second transceivers wirelessly communicates with a stationary unit mounted in a room of a healthcare facility. The controller transmits audio signals from the patient support apparatus to the stationary unit and is adapted to initially attempt to transmit the audio signals to the stationary unit via the first transceiver and, if the initial attempt is unsuccessful, to subsequently attempt to transmit the audio signals via the second transceiver.

According to other aspects of the present disclosure, the patient support apparatus may further include a wired transceiver adapted to communicate with a nurse call system port mounted to a wall of the room. In such embodiments, the controller is further adapted to transmit the audio signals from the patient support apparatus to the nurse call system port if the initial attempt to transmit the audio signals to the stationary unit using the first transceiver and the subsequent attempt to transmit the audio signals to the stationary unit using the second transceiver are both unsuccessful.

The patient support apparatus may further include a microphone that generates the audio signals in response to the patient speaking into the microphone.

In some embodiments, the first transceiver is a radio frequency (RF) transceiver and the second transceiver is a non-RF transceiver, such as, but not limited to, an infrared transceiver or an optical transceiver.

The controller, in some embodiments, is adapted to maintain heartbeat messages between the patient support apparatus and the stationary unit while the patient support apparatus is positioned in the room. The heartbeat messages are alternated between the first and second transceivers. In some embodiments, the heartbeat messages include a transmission and an acknowledgement, and the controller is adapted to respond to a transmission from the stationary unit received via one of the first and second transceivers with an acknowledgement sent over the other of the first and second transceivers.

The heartbeat messages may also include a counter which the controller increments after sending and/or receiving an acknowledgement.

In some embodiments, the controller is adapted to issue an alert if the heartbeat messages stop.

The controller is adapted to only transmit the audio signals via the first transceiver after pairing the first transceiver and the stationary unit, in some embodiments. The controller may pair the first transceiver and the stationary unit by sending a pairing key to the stationary unit via the second transceiver. According to some aspects, the controller deletes the pairing key from all memory on the patient support apparatus after a communication session between the first transceiver and the stationary unit has ended. According to other aspects, the controller generates the pairing key using a hash function and a plurality of values. The plurality of values may include at least one of the following: a serial number, a Media Access Control (MAC) address, a time, a date, and a location.

In some embodiments, the patient support apparatus further includes a base having a plurality of wheels; a frame on which the support surface is supported; a lift subsystem for raising and lowering the frame with respect to the base; a plurality of siderails positioned adjacent the support surface and movable between raised and lowered positions; and a sensor adapted to detect a parameter relating to a component of the patient support apparatus. The controller transmits the parameter to the stationary unit using the first transceiver, or if the initial attempt is unsuccessful, using the second transceiver.

In still other embodiments, the controller is further adapted to receive caregiver audio signals from a nurse call system in communication with the stationary unit and to forward the caregiver audio signals to a speaker onboard the patient support apparatus. The controller receives the caregiver audio signals via the first transceiver, or if the initial attempt is unsuccessful, via the second transceiver.

According to another embodiment of the present disclosure, a patient support apparatus is provided that includes a support surface, a first transceiver, a second transceiver, and a controller. The support surface is adapted to support a patient thereon. The first and second transceivers wirelessly communicate with a stationary unit mounted in a room of a healthcare facility. The controller transmits audio signals from the patient support apparatus to the stationary unit and exchanges heartbeat messages with the stationary unit. The controller exchanges heartbeat messages by alternating the heartbeat messages between the first and second transceivers.

According to other aspects, each of the heartbeat messages includes a transmission and an acknowledgement, and the controller is adapted to respond to a transmission from the stationary unit received via one of the first and second transceivers with an acknowledgement sent over the other of the first and second transceivers. Additionally, or alternatively, each of the heartbeat messages includes a counter and the controller is adapted to increment the counter after sending an acknowledgement.

The controller may be adapted to issue an alert if the heartbeat messages stop.

The controller, in some embodiments, is adapted to only transmit the audio signals via the first transceiver after pairing the first transceiver and the stationary unit. The pairing takes place by sending a pairing key to the stationary unit via the second transceiver.

According to another embodiment of the present disclosure, a patient support apparatus is provided that includes a support surface, a first transceiver, a second transceiver, and a controller. The support surface is adapted to support a patient thereon. The first and second transceivers wirelessly communicate with a stationary unit mounted in a room of a healthcare facility. The controller pairs the first transceiver with the stationary unit by sending a pairing key to the stationary unit via the second transceiver. Thereafter, the controller transmits audio signals from the patient support apparatus to the stationary unit via the first transceiver.

According to other aspects, the controller generates the pairing key using a hash function and a plurality of values. The plurality of values may include at least one of the following: a serial number, a Media Access Control (MAC) address, a time, a date, and a location.

In some embodiments, the controller changes the pairing key each time the first transceiver pairs with the stationary unit. Alternatively or additionally, the controller may delete the pairing key from all memory on the patient support apparatus after a communication session between the first transceiver and the stationary unit has ended.

According to another embodiment of the present disclosure, a patient support apparatus is provided that includes a support surface, a microphone, a first wireless transceiver, a wired transceiver, and a controller. The support surface is adapted to support a patient thereon. The microphone generates audio signals in response to the patient speaking into the microphone. The first wireless transceiver communicates the audio signals to a stationary unit mounted in a room of a healthcare facility if the stationary unit is present. The wired transceiver communicates with a nurse call system port. The controller determines if the stationary unit is present in the room by sending a message to the stationary unit using the first wireless transceiver and analyzing a reply, if any, from the stationary unit. The controller also automatically transmits the audio signals using the first wireless transceiver if the stationary unit is present and automatically transmits the audio signals using the wired transceiver if the stationary unit is not present.

According to other aspects, the patient support apparatus further includes a second wireless transceiver and the controller also uses the second wireless transceiver to determine if the stationary unit is present in the room.

In some embodiments, the patient support apparatus further includes a sensor adapted to detect if the wired transceiver is coupled to the nurse call system port. The sensor detects a voltage supplied by the nurse call system port when the wired transceiver is coupled to the nurse call system port.

The controller may be adapted to conclude the stationary unit is not in the room only if neither of the first and second wireless transceivers is able to establish communications with the stationary unit.

The nurse call system port may be a multi-pin receptacle adapted to receive a cable having a multi-pin connector.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration is used in the description herein of various embodiments (e.g. first, second, third, etc.). Unless otherwise expressly stated, the use of this enumeration should not be construed as limiting the claims to any specific order or number of components, and the use of this enumeration in the written description does not necessarily mean the same enumeration is used in the claims. The use of enumeration should also not be construed as excluding from the scope of the claims any additional steps or components that might be combined with or into the enumerated steps or components.

DETAILED DESCRIPTION OF THE EMBODIMENTS

Figure 1:
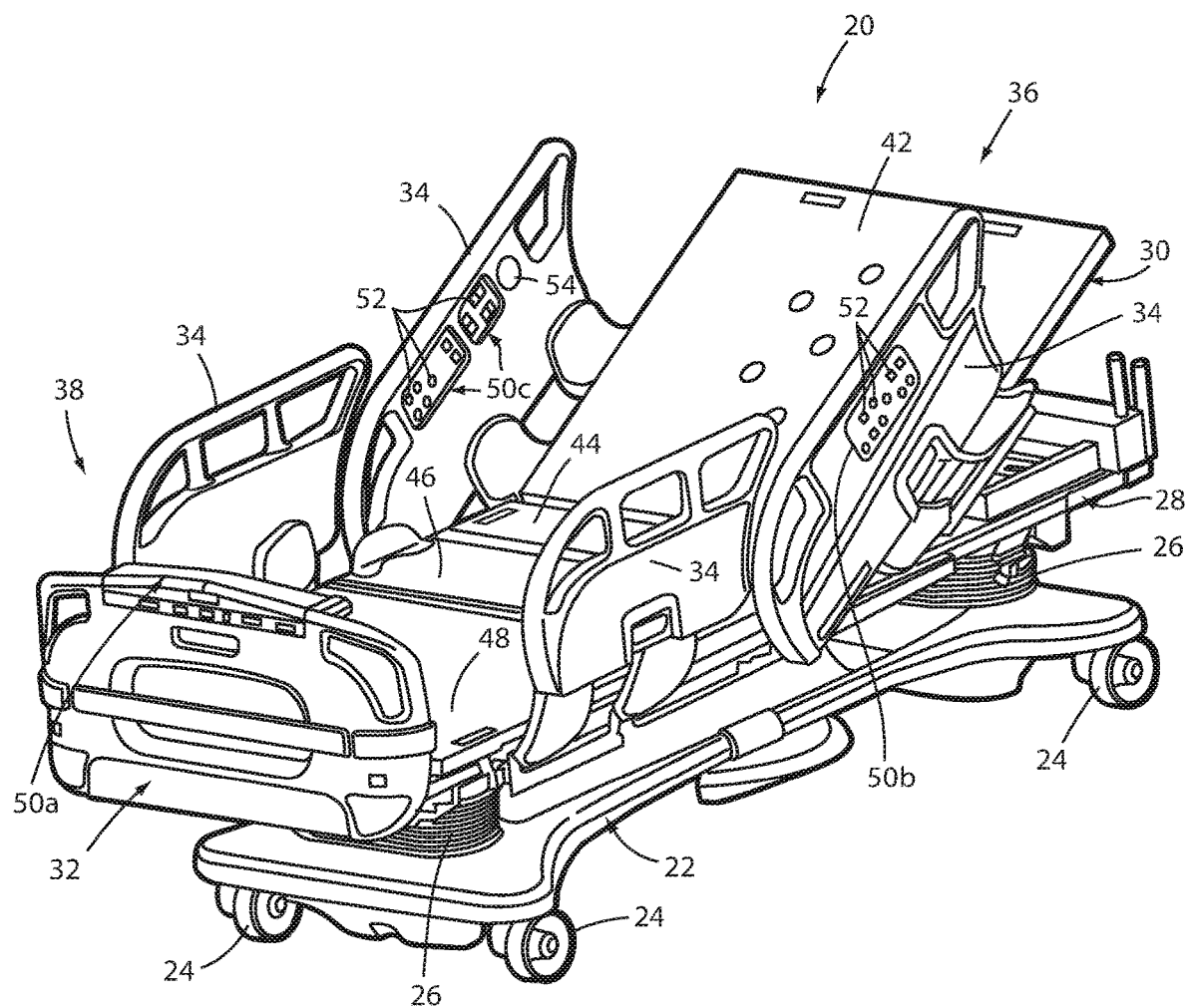
FIG. 1 is a perspective view of a patient support apparatus according to a first embodiment of the disclosure.

An illustrative patient support apparatus 20 according to a first embodiment of the present disclosure is shown in FIG. 1. Although the particular form of patient support apparatus 20 illustrated in FIG. 1 is a bed adapted for use in a hospital or other medical setting, it will be understood that patient support apparatus 20 could, in different embodiments, be a cot, a stretcher, a recliner, a wheelchair, or any other mobile structure capable of supporting a patient in a healthcare environment.

In general, patient support apparatus 20 includes a base 22 having a plurality of wheels 24, a pair of lifts 26 supported on the base 22, a litter frame 28 supported on the lifts 26, and a support deck 30 supported on the litter frame 28. Patient support apparatus 20 further includes a footboard 32 (which may be removable) and a plurality of siderails 34. Siderails 34 are all shown in a raised position in FIG. 1 but are each individually movable to a lower position in which ingress into, and egress out of, patient support apparatus 20 is not obstructed by the lowered siderails 34.

Lifts 26 are adapted to raise and lower litter frame 28 with respect to base 22. Lifts 26 may be hydraulic actuators, pneumatic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 36 and a foot end 38, each of whose height can be independently adjusted by the nearest lift 26. Patient support apparatus 20 is designed so that when a person lies thereon, his or her head will be positioned adjacent head end 36 and his or her feet will be positioned adjacent foot end 38.

Litter frame 28 provides a structure for supporting support deck 30, footboard 32, and siderails 34. Support deck 30 provides a support surface for a mattress 40 (FIG. 2), such as, but not limited to, an air, fluid, or gel mattress. Alternatively, another type of soft cushion may be supported on support deck 30 so that a person may comfortably lie and/or sit thereon. The top surface of the mattress or other cushion forms a support surface for the patient. Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

Patient support apparatus 20 further includes a plurality of user interfaces 50 that enable a user of patient support apparatus 20, such as a patient and/or an associated caregiver, to control one or more aspects of patient support apparatus 20. In the embodiment shown in FIG. 1, patient support apparatus 20 includes a footboard user interface 50a, a pair of outer siderail user interfaces 50b (only one of which is visible), and a pair of inner siderail user interfaces 50c (only one of which is visible). Footboard user interface 50a and outer siderail user interfaces 50b are intended to be used by caregivers, or other authorized personnel, while inner siderail user interfaces 50c are intended to be used by the patient associated with patient support apparatus 20. Each of the user interfaces 50 includes a plurality of controls 52, although each user interface 50 does not necessarily include the same controls 52 and/or functionality. In the illustrated embodiment, footboard user interface 50a includes a substantially complete set of controls for controlling patient support apparatus 20 while user interfaces 50b and 50c include a selected subset of those controls.

Among other functions, the controls 52 of user interfaces 50 allow a user to control one or more of the following: change a height of support deck 30, raise or lower head section 42, activate and deactivate a brake for wheels 24, arm and disarm an exit detection system and, as will be explained in greater detail below, communicate with the particular IT infrastructure installed in the healthcare facility in which patient support apparatus 20 is positioned. Inner siderail user interfaces 50c also include at least one control 52 that enables a patient to call a remotely located nurse (or other caregiver). In addition to the nurse call control, inner siderail user interfaces 50c also include a speaker 54 that enables the patient to hear the nurse's voice and a microphone (not shown) that converts the patient's voice to audio signals that are transmitted to the nurse. In some embodiments, the nurse call control, speaker 54, and microphone are built into a handheld pendant that rests on patient support apparatus 20 and that allows the patient to call and communicate with a remote nurse.

Footboard user interface 50a is implemented in the embodiment shown in FIG. 1 as a control panel having a lid (flipped down in FIG. 1) underneath which is positioned a plurality of controls. As with all of the controls 52 of the various user interfaces 50, the controls of user interface 50a may be implemented as buttons, dials, switches, or other devices. Any of user interfaces 50a-c may also include a display for displaying information regarding patient support apparatus 20. The display is a touchscreen in some embodiments.

Patient support apparatus 20 may be mechanically constructed in a variety of different way and implement a wide variety of additional functionality beyond that explicitly described herein. Some suitable examples of such mechanical functionality and/or additional functionality are found in the following references, all of which are incorporated herein by reference in their entirety: the Stryker Maintenance Manual for the MedSurg Bed, Model 3002 S3, published in 2010 by Stryker Corporation of Kalamazoo, Mich., U.S. Pat. No. 8,689,376 issued Apr. 8, 2014 by inventors David Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION; U.S. patent application Ser. No. 13/775,285 filed Feb. 25, 2013 by inventors Guy Lemire et al. and entitled HOSPITAL BED; and U.S. patent application Ser. No. 14/212,009 filed Mar. 14, 2014 by inventors Christopher Hough et al., and entitled MEDICAL SUPPORT APPARATUS. The mechanical construction of patient support apparatus 20 may also take on forms different from what is disclosed in the aforementioned references, and patient support apparatus 20 may include still other functionality.

Figure 2:
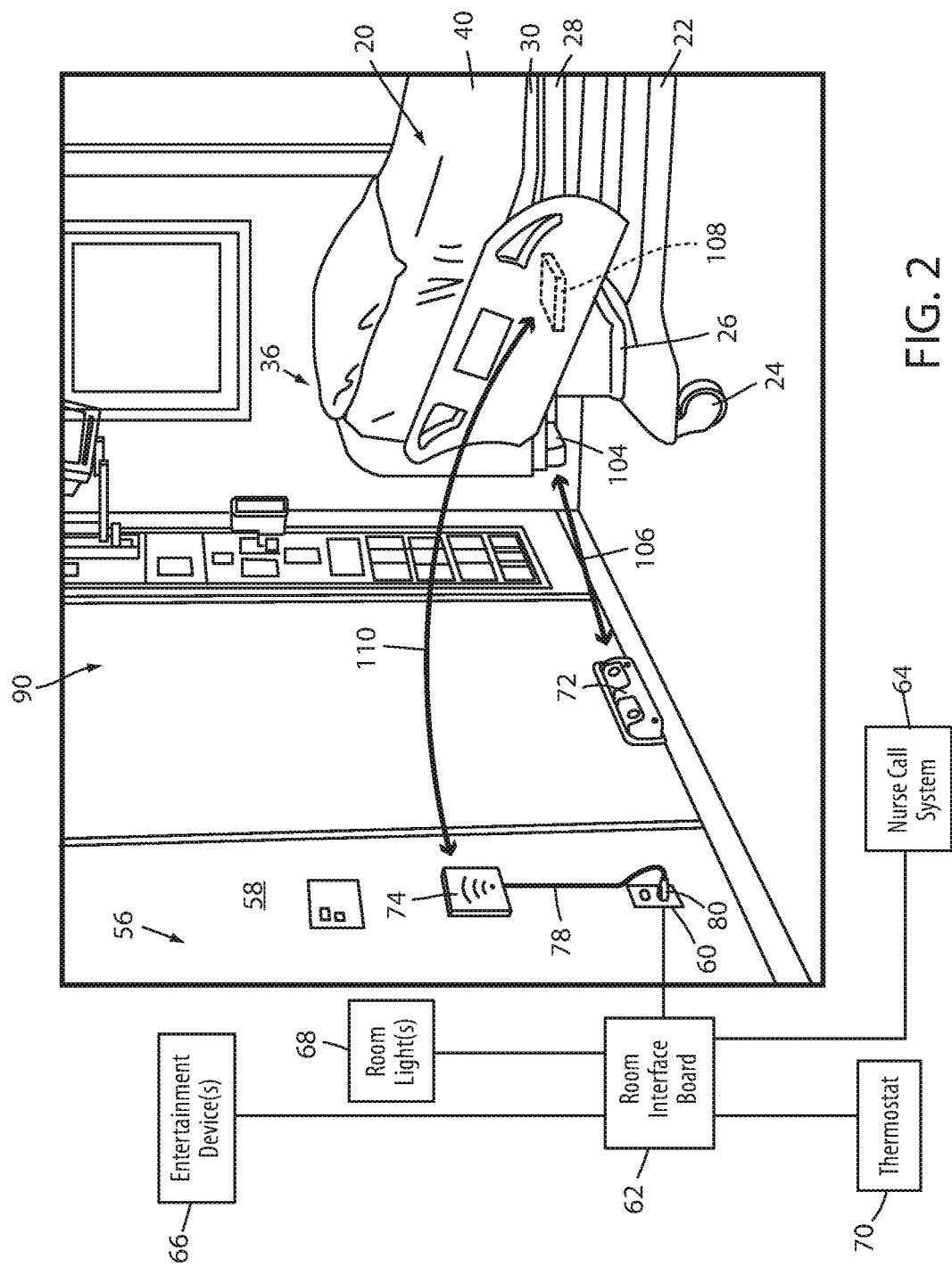
FIG. 2 is a perspective view of the patient support apparatus of FIG. 1 shown in a hospital room adjacent a headwall unit comprised of separate first and second transceivers.

FIG. 2 illustrates patient support apparatus 20 coupled to the IT infrastructure 56 of an illustrative healthcare facility according to one common configuration. As shown therein, the healthcare facility includes a headwall 58, a cable port 60 mounted to the headwall 58, a room interface board 62 in communication with cable port 60, and a plurality devices and components in communication with the room interface board 62, such as a nurse call system 64, one or more entertainment devices 66, one or more room lights 68, and a thermostat 70. Cable port 60, room interface board 62, nurse call system 64, entertainment devices 66, room lights 68, and thermostat 70 may all be conventional pre-existing components that are installed in the healthcare facility independently of patient support apparatus 20 and its associated headwall units 76, as will be discussed in more detail below. Cable port 60 is sometimes referred to as a nurse call system port, although it communicates with more than just nurse call system 64. Additional IT infrastructure beyond what is shown in FIG. 2 may also be present in the healthcare facility, some examples of which are discussed in more detail below with respect to FIGS. 4 & 5.

Nurse call system 64 may be a conventional nurse call system having one or more nurses' stations positioned throughout the healthcare facility. Nurse call system 64 routes patient calls from patient support apparatus 20 to one or more nurses' stations so that the patient is able to speak with a remotely positioned nurse at a nurses' station while the patient is supported on patient support apparatus 20, as is known in the art.

Entertainment devices 66 are conventional entertainment equipment that may be present in the particular room in which patient support apparatus 20 is located. Such entertainment equipment may include a television, video recorder, radio, etc., and/or other device whose volume, channel, power, and other aspects can be controlled via commands from room interface board 62.

Room lights 68 provide lighting to one or more sections of the room in which patient support apparatus 20 is located. Room lights 68 may be conventional overhead lights and/or one or more night lights or other more localized lights within the room.

Thermostat 70 controls the temperature of the room and/or a portion of the room (e.g. a particular bay) in which patient support apparatus 20 is located. Thermostat 70 is in communication with a conventional Heating, Ventilation, and Air Conditioning (HVAC) system.

Figure 4:
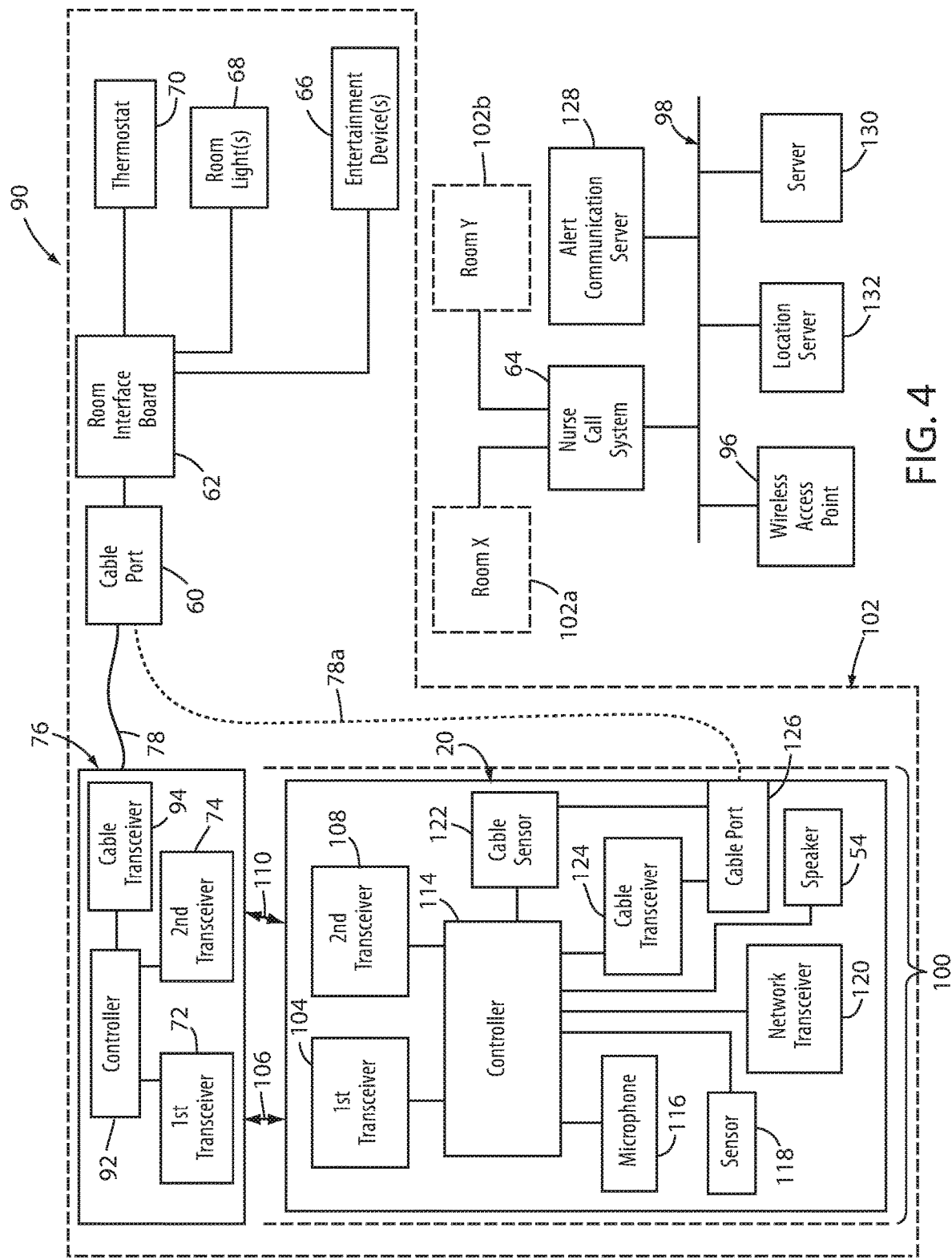
FIG. 4 is a block diagram one embodiment of a headwall system incorporating the headwall unit of FIG. 2.

Patient support apparatus 20 is adapted to wirelessly communicate with a first transceiver 72 and a second transceiver 74. First and second transceivers 72 and 74 together form a headwall unit 76. In the embodiment shown in FIG. 1, first and second transceivers 72 and 74 are two wall units. In other embodiments, such as shown in FIG. 4, transceivers 72 and 74 are combined into a single wall unit having a single housing, as discussed in more detail below. Regardless of whether coupled together in a single housing or separated into two physically disparate units, first and second transceivers 72 and 74 are adapted to communicate with each other, in at least some embodiments. Such communication takes place via a wired connection when transceivers 72 and 74 are combined in a single housing, and may take place wirelessly when transceivers 72 and 74 are physically separated.

Second transceiver 74 includes a cable 78 that is coupled to cable port 60 (FIG. 2). Cable 78 allows second transceiver 74 to communicate with cable port 60 and all of the components in communication with cable port 60 (e.g. nurse call system 64, room interface board 62, etc.). Cable 78 includes a connector 80 that is adapted to mate with cable port 60. Connector 80 may vary from room to room and from healthcare facility to healthcare facility depending upon the particular type of cable port 60 that is installed within a particular room of a particular healthcare facility. In the embodiment of second transceiver 74 shown in FIG. 2 (and FIG. 3), second transceiver 74 further includes a controller and a cable transceiver for facilitating communications between patient support apparatus 20 and cable port 60. The cable transceiver and controller are described in more detail below with respect to a headwall unit 76 that incorporates both first and second transceiver 72 and 74 into a common housing.

Figure 3:
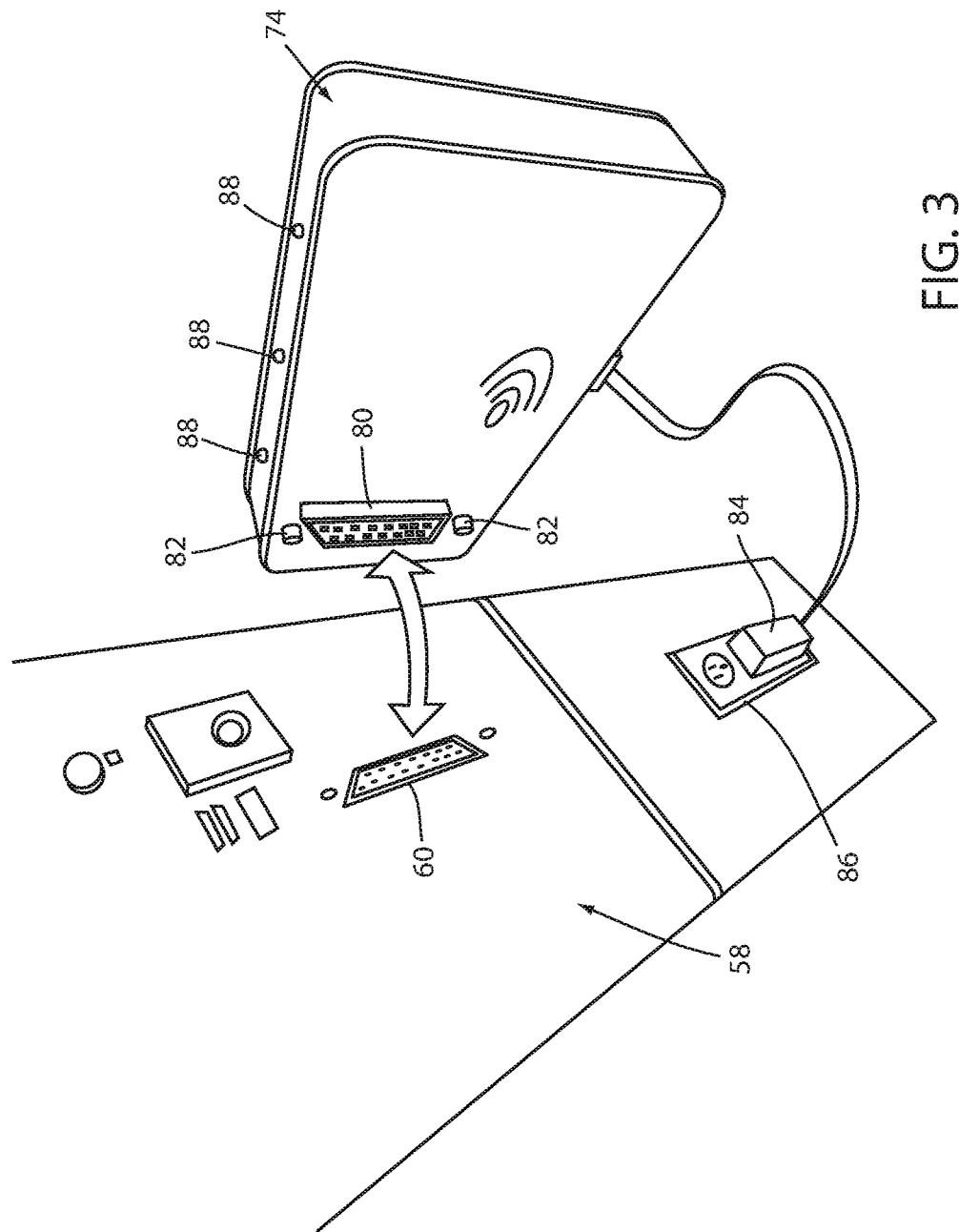
FIG. 3 is perspective view of an alternative embodiment of the second transceiver of FIG. 2.

FIG. 3 illustrates an alternative embodiment of second transceiver 74 in which cable 78 has been omitted. In this embodiment, second transceiver 74 has connector 80 integrated therein and second transceiver 74 couples directly to cable port 60. Connector 80 is adapted to be inserted into cable port 60, which is a conventional cable interface that exists within a medical facility. Cable port 60 is a receptacle that is dimensioned and shaped to selectively frictionally retain connector 80 therein and to support the entire second transceiver 74. One or more alignment posts 82 may be included with connector 80 in order to more securely retain second transceiver 74 to cable port 60, if desired.

In the embodiment shown in FIG. 3, connector 80 is a 37 pin connector that includes 37 pins adapted to be inserted into 37 mating sockets of cable port 60. Such 37 pin connections are one of the most common types of connectors found on existing headwalls of medical facilities for making connections to the nurse call system 64 and/or the room interface board 62. Connectors 80 of FIGS. 2 and 3 are therefore configured to mate with one of the most common type of cable ports 60 used in medical facilities. Such 37 pin connectors, however, are not the only type of connectors, and it will be understood that second transceiver 74 can utilize different types of connectors 80 (whether integrated therein or attached to cable 78) that are adapted to electrically couple to different types of cable ports 60. One example of such an alternative cable port 60 and cable is disclosed in commonly assigned U.S. patent application Ser. No. 14/819,844 filed Aug. 6, 2015 by inventors Krishna Bhimavarapu et al. and entitled PATIENT SUPPORT APPARATUSES WITH WIRELESS HEADWALL COMMUNICATION, the complete disclosure of which is incorporated herein by reference. Still other types of cable ports 60 and corresponding cable connectors 80 may be utilized.

In the embodiment shown in FIG. 3, second transceiver 74 includes an electrical plug 84 adapted to be inserted into a conventional electrical outlet 86. Electrical plug 84 enables second transceiver 74 to receive power from the mains electrical supply via outlet 86. It will be appreciated that, in some embodiments, second transceiver 74 is battery operated and plug 84 may be omitted. In still other embodiments, second transceiver 74 may be both battery operated and include plug 84 so that in the event of a power failure, battery power supplies power to second transceiver 74, and/or in the event of a battery failure, electrical power is received through outlet 86. Although not shown, first transceiver 72 may also include an electrical plug for receiving power, may be battery operated, and/or may be both battery operated and include an electrical plug.

The embodiment of second transceiver 74 shown in FIG. 3 also includes a plurality of status lights 88. Status lights 88 provide visual indications about one or more aspects of second transceiver 74. For example, in some embodiments, the illumination of one of status lights 88 indicates that second transceiver 74 is in successful communication with room interface board 62 and/or patient support apparatus 20. The illumination of one or more additional status lights 88 may also or alternatively indicate that power is being supplied to second transceiver 74 and/or the status of a battery included within second transceiver 74.

Headwall unit 76 (FIG. 4) is adapted to wirelessly receive signals from patient support apparatus 20 and deliver the signals to cable port 60 in a manner that matches the way the signals would otherwise be delivered to cable port 60 if a conventional nurse call cable were connected between patient support apparatus 20 and cable port 60. In other words, patient support apparatus 20 and headwall unit 76 cooperate to provide signals to cable port 60 in a manner that is transparent to cable port 60 and room interface board 62 such that these components cannot detect whether they are in communication with patient support apparatus 20 via wired or wireless communication. In this manner, a healthcare facility can utilize the wireless communication abilities of one or more patient support apparatuses 20 without having to make any changes to their existing cable ports 60 (or to their nurse call system 64 or room interface boards 62).

In addition to sending signals received from patient support apparatus 20 to cable port 60, headwall unit 76 is also adapted to forward signals received from cable port 60 to patient support apparatus 20. Headwall unit 76 is therefore adapted to provide bidirectional communication between patient support apparatus 20 and cable port 60. Such bidirectional communication includes, but is not limited to, communicating audio signals between a person supported on patient support apparatus 20 and a caregiver positioned remotely from patient support apparatus 20. The audio signals received by headwall unit 76 from patient support apparatus 20 are forwarded to cable port 60, and the audio signals received from cable port 60 are forwarded to patient support apparatus 20.

Headwall unit 76 communicates the data and signals it receives from patient support apparatus 20 to room interface board 62 by utilizing a cable transceiver 94 (discussed more below with respect to FIG. 4) that directs the incoming data and signals headwall unit 76 from patient support apparatus 20 to the appropriate pin or pins of cable port 60. For example, when cable port 60 includes 37 sockets for coupling to a 37 pin plug, it is common for pins #30 and #31 to be used for indicating a "priority alert," which is often synonymous with an alert that is issued when a patient exits from patient support apparatus 20. Further, depending upon the particular configuration that has been implemented at a particular healthcare facility, the connection between pins #30 and #31 may be normally open or it may be normally closed. Regardless of whether it is normally open or normally closed, whenever headwall unit 76 receives a message from patient support apparatus 20 that a person has exited from patient support apparatus 20, headwall unit 76 utilizes cable transceiver 94 to change the status of pins #30 and #31 such that they switch from whatever state they are normally in to their opposite state. Headwall unit 76 therefore reacts to the exit message it receives from patient support apparatus 20 by either opening or closing pins #30 and #31. The nurse call system 64 that is communicatively coupled to cable port 60 interprets this opening or closing of pins #30 and #31 in the same manner as if a cable were coupled between cable port 60, such as by sending the appropriate signals to one or more nurse's stations, flashing a light outside the room of patient support apparatus 20, forwarding a call to a mobile communication device carried by the caregiver assigned to the patient of patient support apparatus 20, and/or taking other steps, depending upon the specific configuration of the nurse call system.

In addition to sending data indicating that a patient of patient support apparatus 20 has exited, or is about to exit, therefrom, patient support apparatus 20 is configured, in at least one embodiment, to wirelessly send to headwall unit 76 any one or more of the following additional messages: heartbeat messages and acknowledgements thereof; messages to turn on or off one or more room lights; messages to turn on or off one or more reading lights; messages to increase or decrease the volume of a nearby television set or radio; messages to change a channel of the nearby television set or radio; messages containing audio packets generated from one or more microphones on the patient support apparatus 20 into which the patient of patient support apparatus 20 speaks when desiring to communicate with a remote caregiver; messages indicating the current status of one or more siderails 34 of patient support apparatus 20 (e.g. whether the side rails are up or down, or have changed position); messages indicating the current status of a brake on patient support apparatus 20; messages indicating the current status of the height of support deck 30 relative to base 22 (e.g. such as whether support deck 30 is at its lowest height or not); messages indicating the current angle of head section 42; messages indicating the current status of an exit detection system (e.g. whether the exit detection system is armed or not); messages indicating the current charging status of one or more batteries on patient support apparatus 20; messages indicating the current status of an alternating current (A/C) power cable on patient support apparatus 20 (e.g. whether it is plugged in or not); diagnostic information about patient support apparatus 20; messages containing patient data gathered from one or more sensors on board patient support apparatus 20; message containing patient data gathered from one or more medical devices that are separate from patient support apparatus 20 but which communicate such data to patient support apparatus 20; and/or any other messages containing information about patient support apparatus 20, the patient supported thereon, and/or a caregiver associated with the patient.

In at least one embodiment, headwall unit 76 is further configured to transmit information to cable port 60 that does not originate from patient support apparatus 20, but instead is generated internally within headwall unit 76. For example, in one embodiment, headwall unit 76 is adapted to forward to cable port 60 a signal that indicates a "cord-out" alert whenever the communication link between headwall unit 76 and patient support apparatus 20 is unintentionally lost. In many instances, when a conventional cable is coupled between cable port 60 and a hospital bed, and the cable is inadvertently disconnected, the electrical status of pins 10 and 11 (in a conventional 37 pin connection) will be changed such that the nurse call system will recognize that the cable has become disconnected, and will therefore issue an appropriate alert to the appropriate personnel. Headwall unit 76 is configured to make the same changes to pins 10 and 11 when it unintentionally loses communication with patient support apparatus 20 that would be made to pins 10 and 11 if a cable connection between patient support apparatus 20 and cable port 60 were to become unintentionally disconnected. Thus, headwall unit 76 and patient support apparatus 20 together include the same ability to provide an indication to cable port 60 of an unintentional disconnection that exists in some currently-available cable connections to cable interfaces. Still other types of signals that originate from within headwall unit 76 may also be sent to cable port 60 in addition to, or in lieu of, this cord-out alert.

In addition to forwarding any of the above-described messages or signals to cable port 60, headwall unit 76 is also adapted, in at least one embodiment, to forward the following messages to patient support apparatus 20 based on information it receives from devices in communication with cable port 60: messages indicating the establishment and disestablishment of a nurse-call communication link (e.g. messages used for turning on and off a "nurse answer" light on patient support apparatus 20); and messages containing audio packets of a caregiver's voice (generated from a microphone into which the caregiver speaks and forwarded to the appropriate pins of cable port 60).

In other embodiments, one or more additional messages are also transmitted to patient support apparatus 20 that originate from within headwall unit 76, rather than from any of the devices in communication with cable port 60. Such messages include any one or more of the following: the charge status of a battery within headwall unit 76, or a battery inside first transceiver 72; acknowledgements of messages transmitted from patient support apparatus 20 to headwall unit 76; heartbeat messages and acknowledgements thereof; and messages used to establish and disestablish the communication link(s) between headwall unit 76 and patient support apparatus 20. Still other messages communicated to and/or from headwall unit 76 will be discussed in greater detail below.

As was noted previously, first transceiver 72 and second transceiver 74 may be integrated into a single housing, in some embodiments. FIG. 4 illustrates one such embodiment. FIG. 4 illustrates a headwall system 90 in which headwall unit 76 includes both first transceiver 72 and second transceiver 74, as well as a controller 92 and a cable transceiver 94.

Controller 92 is a conventional microcontroller, in at least one embodiment. In general, controller 92 includes any and all electrical circuitry and components necessary to carry out the functions and algorithms described herein, as would be known to one of ordinary skill in the art. Such circuitry may include one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions within headwall unit 76, or they may reside in a common location within headwall unit 76. When physically distributed, the components may communicate using any suitable serial or parallel communication protocol, such as, but not limited to, CAN, LIN, Firewire, I-squared-C, RS-232, RS-465, universal serial bus (USB), etc. The instructions followed by controller 92 in carrying out the functions described herein, as well as the data necessary for carrying out these functions, are stored in one or more accessible memories, such as, but not limited to, a memory (not shown) contained within headwall unit 76.

Cable transceiver 94 (FIG. 4) is adapted to communicate with cable 78 and the cable port 60 to which the cable 78 is coupled. Cable transceiver 94 therefore converts messages from controller 92 into the proper form to match the communication characteristics of cable port 60. In this regard, cable transceiver 94 selects which pin of the multiple pins certain data is to be communicated over and/or converts the data into the proper format and/or protocol for communicating with room interface board 62 and the devices in communication with room interface board 62. Cable transceiver 94 also converts messages and/or signals received from room interface board 62 into a format compatible with controller 92 so that controller 92 may process the messages and/or signals from room interface board 62 in the proper manner.

In some embodiments, headwall unit 76 may include additional components, including, but not limited to, a network transceiver, an auxiliary transceiver, a caregiver presence detector, and an additional cable port. If included, the network transceiver is adapted to communicate with one or more wireless access points 96 of healthcare facility network 98. The network transceiver may be a WiFi transceiver (IEEE 802.11) adapted to communicate with access points 96 using any of the various WiFi protocols (IEEE 802.11b, 801.11g, 802.11n, 802.11ac . . . , etc.), or it may be a transceiver adapted to communicate using any of the frequencies, protocols, and/or standards disclosed in commonly assigned U.S. patent application Ser. No. 62/430,500 filed Dec. 6, 2016, by inventor Michael Hayes and entitled NETWORK COMMUNICATION FOR PATIENT SUPPORT APPARATUSES, the complete disclosure of which is incorporated herein by reference. Still other types of network transceivers may be used.

In those embodiments of headwall unit 76 that include an auxiliary transceiver, a caregiver presence detector, and/or an additional cable port, the functions and construction of these components may be implemented in accordance with the auxiliary transceiver, caregiver presence detector, and cable port disclosed in headwall unit 66 of commonly assigned U.S. patent application Ser. No. 62/600,000 filed Dec. 18, 2017, by inventors Alex Bodurka et al., and entitled SMART HOSPITAL HEADWALL SYSTEM, the complete disclosure of which is incorporated herein by reference.

Headwall unit 76 is typically positioned at the head of a bay area 100 (FIG. 4), which is the area where the patient support apparatus 20 typically remains when it is positioned within a particular room 102 of the healthcare facility. In some healthcare facilities, one or more of the rooms are single patient support apparatus rooms in which only a single patient support apparatus is present (private rooms). In such rooms, there is only one bay 100. Healthcare facilities, however, typically include one or more rooms in which multiple patient support apparatuses 20 are positioned (semi-private rooms). In such rooms, there are multiple bays 100 for the multiple patient support apparatuses 20.

First wireless transceiver 72 of headwall unit 76, in the illustrated embodiment, is an infrared transceiver and is adapted to communicate with a first wireless transceiver 104 of patient support apparatus 20. First wireless transceivers 72 and 104 are adapted to establish a communication link 106 (FIG. 2) only when patient support apparatus 20 is positioned within close proximity to headwall unit 76, such as when patient support apparatus 20 is positioned within the particular bay area 100 associated with that particular headwall unit 76. In other embodiments, it will be understood that first wireless transceiver 72 of headwall unit 76 may be implemented using short range communication media and/or protocols other than infrared communications, including, but not limited to, optical communications.

Second transceiver 74 of headwall unit 76 is adapted to communicate with a second transceiver 108 (FIG. 4) of patient support apparatus 20. Second transceivers 74 and 108 are adapted to establish a second communication link 110 (FIG. 2). Second transceiver 74 of headwall unit 76 is adapted to communicate with patient support apparatus 20 using Radio Frequency (RF) communications that are not line-of-sight, unlike the IR communications of first transceiver 72. In some embodiments, second transceivers 74 and 108 are Bluetooth transceivers configured to communicate using one or more of the Bluetooth standards (e.g. IEEE 802.14.1 or any of the standards developed by the Bluetooth Special Interest Group). It will be understood, however, that in other embodiments, second transceivers 74 and 108 may utilize other forms of Radio Frequency (RF) and non-RF communication. For purposes of the following written description it will be assumed that second transceivers 74 and 108 communicate using conventional Bluetooth technology, although this written description is not meant to be an indication that other types of communication cannot be used between second transceivers 74 and 108.

Each headwall unit 76 includes a unique identifier 112 that uniquely identifies that particular headwall unit 76 from the other headwall units 76 within the healthcare facility. This unique identifier is used by patient support apparatus 20 and/or other devices in communication with first transceiver 72 of headwall unit 76 to determine their location within a particular healthcare facility. When first transceiver 72 is able to communicate with patient support apparatus 20, controller 92 of headwall unit 76 transmits the unique identifier 112 to the patient support apparatus 20 (or other device). In the embodiment shown, unique identifier 112 is only used for location purposes when it is sent via first transceiver 72. It will be understood, however, that second transceiver 74 may transmit identifier 112 to the patient support apparatus 20 for other non-location-determining purposes.

In order to determine location from the unique identifier 112, a controller on board patient support apparatus 20 (discussed more below) sends the unique identifier to one or more servers on a healthcare facility computer network 98, and the server converts the identifier into a location via a look-up table that correlates all of the headwall unit identifiers 112 within the healthcare facility to their respective locations. Alternatively, the controller on board patient support apparatus 20 consults an on-board look-up table that correlates the unique identifiers to locations within the healthcare facility and the controller determines the location of patient support apparatus 20 via the look-up table. In still another embodiment, unique identifier 112 identifies directly the room number in which headwall unit 76 is positioned, as well as the bay area 100 associated with headwall unit 76, and none of the receiving devices of the identifier 112 (e.g. patient support apparatus 20) have to consult a look-up table to convert the ID 112 into a location, but instead are able to determine their location directly from the ID 112.

In some embodiments, first transceiver 72 is used by headwall unit 76 to establish and periodically verify that patient support apparatus 20 (and/or other devices) are within bay area 100, while second transceiver 74 is used to communicate information back and forth between headwall unit 76 and patient support apparatus 20 (and other devices within the room). In such embodiments, first transceiver 72 may be used in situations where second transceiver is blocked or otherwise not functional. In still other modified embodiments, first transceiver 72 may be used to communicate data in addition to the location identifier 112, as well as to perform other functions besides establishing and verifying the presence of patient support apparatus 20 and/or other devices within bay area 100.

In addition to other communications, first and second transceivers 72 and 74 are utilized by controller 92 of headwall unit 76 to communicate information wirelessly to patient support apparatus 20 and to receive information wirelessly from patient support apparatus 20. In many situations, the information received from patient support apparatus 20 is forwarded to room interface board 62 via cable transceiver 124 and cable port 60. Room interface board 62, in turn, forwards the information to nurse call system 64 and/or other devices in communication with room interface board 62.

When patient support apparatus 20 is positioned within a bay 100 and in normal communication with headwall unit 76, both of the transceivers 72 and 74 are in communication with patient support apparatus 20. If patient support apparatus 20 is positioned outside of the bay area 100, first transceiver 72 will not be able to communicate with patient support apparatus 20 because first transceiver 72 uses infrared signals, which are line-of-sight signals, and first transceiver 72 is set up such that its line-of-sight signals are only detectable by the patient support apparatus 20 when the patient support apparatus 20 is positioned within the corresponding bay 100, or a portion of that bay 100. Accordingly, when controller 92 determines that first transceiver 72 is able to successfully communicate with a patient support apparatus 20, it concludes that the patient support apparatus 20 is positioned adjacent to the headwall unit 76.

Second transceiver 74 is able to communicate with patient support apparatus 20 when patient support apparatus 20 is positioned outside of bay area 100 because second transceiver 74 is a Bluetooth transceiver that uses radio frequency (RF) waves that are not line-of-sight. Accordingly, patient support apparatus 20 does not need to be in bay area 100 to communicate with second transceiver 74. However, the power levels of the Bluetooth communication used by second transceiver 74 are set such that patient support apparatus 20 is not generally able to communicate with second transceiver 74 when it is positioned outside of the room in which the headwall unit 76 is positioned. As a result, when controller 92 establishes communication with any patient support apparatus 20 via second transceiver 74, controller 92 knows that the patient support apparatus 20 is currently positioned within the same room as the headwall unit 76 (or very close to the room). Further, when controller 92 establishes communication with patient support apparatus 20 using first transceiver 72, controller 92 knows that patient support apparatus 20 is currently positioned within the bay area 100, and controller 92 is thereby able to confirm its position within a particular room using two sources of information.

Patient support apparatus 20 (FIG. 4) also includes a controller 114 in communication with first and second transceivers 104 and 108, a microphone 116, one or more sensors 118, a network transceiver 120, a cable sensor 122, and a cable transceiver 124. Controller 114, like controller 92 of headwall unit 76, includes any and all electrical circuitry and components necessary to carry out the functions and algorithms described herein, as would be known to one of ordinary skill in the art. Generally speaking, controller 114 may include one or more microcontrollers, microprocessors, and/or other programmable electronics that are programmed to carry out the functions described herein. The other electronic components may include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions within patient support apparatus 20, or they may reside in a common location within patient support apparatus 20. When physically distributed, the components may communicate using any suitable serial or parallel communication protocol, such as, but not limited to, CAN, LIN, Firewire, I-squared-C, RS-232, RS-465, universal serial bus (USB), etc. The instructions followed by controller 114 in carrying out the functions described herein, as well as the data necessary for carrying out these functions, are stored in one or more accessible memories (not shown).

Microphone 116 is adapted to convert voice sound waves from a patient positioned on patient support apparatus 20 into audio signals that are sent by patient support apparatus 20 to a remote nurses' station. The audio signals are transmitted, in at least one embodiment, from patient support apparatus 20 to headwall unit 76 via second communization link 110 between second transceivers 74 and 108. Headwall unit 76 forwards the audio signals to nurse call system 64 via cable 78, cable port 60, and room interface board 62. Patient support apparatus 20 receives audio signals from the nurse call system 64 via second communication link 110 and forwards them to speaker 54. Speaker 54 converts the audio signals into sound waves which can be heard by the patient on patient support apparatus 20.

Sensors 118 may include a variety of different types of sensors adapted to detect parameters relating to patient support apparatus 20, a patient associated with patient support apparatus 20, a medical device in communication with patient support apparatus 20, and/or other parameters. More specifically, sensors 118 may include, but are not limited to, any one or more of the following: a brake sensor adapted to detect whether or not a caregiver has applied a brake to patient support apparatus 20; a height sensor adapted to detect the height of support deck 30 (and/or detect whether support deck 30 is at its lowest height or not); siderail sensors adapted to detect whether siderails 34 are in their raised or lowered orientations; one or more exit detection sensors adapted to detect when a patient exits from patient support apparatus 20; an exit detection status sensor adapted to detect whether the exit detection system on board patient support apparatus 20 is armed or not; scale sensors adapted to detect a weight of the patient and/or other items on litter frame 28; and/or other types of sensor.

When sensors 118 are part of an exit detection system and/or scale system, sensors 118 may be implemented as one or more load cells that detect the weight and/or center of gravity of the patient. Illustrative manners in which such force sensors can be used to detect the presence and absence of a patient, as well as the center of gravity of the patient, are disclosed in the following commonly assigned U.S. patent references: U.S. Pat. No. 5,276,432 issued to Travis and entitled PATIENT EXIT DETECTION MECHANISM FOR HOSPITAL BED; and U.S. patent application Ser. No. 62/253,167 filed Nov. 10, 2015, by inventors Marko Kostic et al. and entitled PERSON SUPPORT APPARATUSES WITH ACCELERATION DETECTION, the complete disclosures of both of which are incorporated herein by reference. Other types of sensors may be used for detecting a patient's exit and/or weight.

Cable sensor 122 is adapted to detect whether a cable 78a (FIG. 4) is coupled to a cable port 126 of patient support apparatus 20. When such a cable 78a is present, patient support apparatus 20 communicates directly with cable port 60 and room interface board 62 and bypasses headwall unit 76. Cable sensor 122, in at least one embodiment, is implemented as a conventional voltage detector that detects a voltage supplied through the cable when the cable is plugged into cable port 126. The voltage is supplied by the electronics of headwall 58 coupled to room interface board 62 and cable port 60. Thus, when a cable is coupled between patient support apparatus 20 and cable port 60 of headwall 58, the cable will have a non-zero voltage on at least one of the pins of the connector that is coupled to cable port 126 of patient support apparatus 20. Cable sensor 122 detects this voltage (or its absence when the cable is not plugged into patient support apparatus 20, or not coupled at its other end to cable port 60 of headwall 58), and reports the presence/absence of the cable to controller 92. Controller 92 uses this information in any of the manners discussed in greater detail below.

It will be understood that patient support apparatuses 20 include more components than those shown in FIG. 4, and that controller 114 may control more than the components shown in FIG. 4. For example, as noted with respect to FIG. 1, patient support apparatus 20 includes a plurality of user interfaces 50. Those user interfaces may be in direct communication with controller 114 and/or under the control of controller 114, or those user interfaces 50 may be under the control of a separate controller that is, in turn, in communication with controller 114. Patient support apparatus 20 may also include an exit detection system that is under the control of controller 114, or that includes its own controller that communicates with controller 114. One such suitable exit detection system is disclosed in commonly assigned U.S. Pat. No. 5,276,432 issued to Travis and entitled PATIENT EXIT DETECTION MECHANISM FOR HOSPITAL BED, which is incorporated herein by reference, although other types of exit detection systems may be included with patient support apparatus 20. Still other components may be present on patient support apparatus 20 and under the control of controller 114 or another controller onboard patient support apparatus 20.

Patient support apparatus 20 is depicted in FIG. 4 as being located in a particular room 102 of a healthcare facility. The healthcare facility may include additional rooms 102a, 102b, etc. that are similar to room 102. That is, each room may include one or more headwall units 76 where each headwall unit 76 communicates with a cable port 60 and the room interface board 62 for that particular room. The room interface boards 62, in turn, are in communication with room lights 68 and entertainment devices 66 for that particular room. Still further, each room interface board 62 is coupled to the nurse call system 64. The nurse call system 64, in some embodiments, is in communication with the healthcare facility computer network 98.

Healthcare facility computer network 98 includes a plurality of servers, such as, but not limited to, a caregiver communication server 128, a patient support apparatus/headwall server 130, and a location server 132. Caregiver communication server 128 may be a conventional server that communicates alerts to caregivers carrying wireless electronic devices (e.g. pagers, badges, smart phones, portable computers, etc.). Patient support apparatus/headwall server 130 is a server that receives communications from patient support apparatuses 20 and/or headwall units 76. In some cases, the communications received from patient support apparatuses 20 and/or headwall units 76 are alerts that are intended to be communicated to a caregiver. In such cases, server 130 forwards the alerts to caregiver server 128, which then forwards the alerts to the appropriate personnel.

Location server 132 is adapted to monitor and record the current locations of patient support apparatuses 20, patients, and/or caregivers within the healthcare facility. In the illustrated embodiment of headwall system 90, patient support apparatus 20 determines its location within a facility from its communication with a particular headwall unit 76. More particularly, each patient support apparatus 20 determines its location within the healthcare facility from its ability to communicate with a nearby headwall unit 76 (whose locations are fixed and known) using the short range first transceivers 72 and 104. Location server 132 shares the current location of the patient support apparatuses 20 with other applications/servers on network 98 that request this location information. In some modified embodiments, location server 132 is a conventional asset and tracking server that determines the location of patient support apparatuses 20 without utilizing communication with headwall units 76.

One or more additional servers may also be included, such as, but not limited to, an Internet server and/or an Internet gateway that couples network 98 to the Internet, thereby enabling the servers, headwall units 76, patient support apparatuses 20, and/or other applications on network 98 to communicate with computers outside of the healthcare facility, such as, but not limited to, a geographically remote server operated under the control of the manufacturer of patient support apparatuses 20 and/or headwall units 76. Network 98 may also include a conventional Admission, Discharge, and Tracking (ADT) server that allows patient support apparatuses 20 and/or headwall units 76 to retrieve information identifying the patient assigned to a particular patient support apparatus 20. Still further, healthcare network 98 may further include one or more conventional work flow servers and/or charting servers that assign, monitor, and/or schedule patient-related tasks to particular caregivers. It will also be understood by those skilled in the art that still more modifications to network 98 may be made beyond those listed herein. As but one example, it will be understood that, although FIG. 4 shows nurse call system 64 coupled to network 98, this may be modified. Still other modifications are possible.

Both first and second transceivers 72 and 74 of headwall unit 76 are configured to periodically transmit a beacon signal, such as, but not limited to, once every second or so. When a patient support apparatus 20 moves into the room in which the headwall unit 76 is positioned, the first and second transceivers 104 and 108, respectively, receive the beacon signal and respond thereto. The beacon signal includes an identifier of that particular headwall unit 76 and the patient support apparatus 20 uses the identifier to automatically establish communication links with the headwall unit 76 in response to the beacon signal. That is, headwall unit 76 is configured, in at least some embodiments, to automatically establish communication links 106 and 110 with patient support apparatus 20 when patient support apparatus 20 enters the room.

Communication links 106 and 110 are established automatically without requiring any steps on the part of a caregiver that are specific to this process. In other words, the caregiver does not need to press a button, flip a switch, or manipulate any controls on patient support apparatus 20 or headwall unit 76 to establish links 106 and 110. Instead, the mere positioning of patient support apparatus 20 within range of first and second transceivers 72 and 74 automatically causes patient support apparatus 20 to establish communication links with these devices. The manner in which these links are established and maintained is discussed in more detail below.

In those implementations of headwall system 90 where one or more rooms in a healthcare facility contain multiple headwall units 76, second transceiver 74 may initially establish a communication link 110 with a patient support apparatus 20 when entering a room that is not the patient support apparatus 20 that is ultimately parked in front of second transceiver 74. In other words, when patient support apparatus 20 is initially moved into a room with multiple headwall units 76, the patient support apparatus may be able to communicate with the second transceiver 74 of both headwall units 76. Multiple communication links 110 may therefore be initially established. However, once the patient support apparatus 20 is moved to its intended bay area 100, the patient support apparatus 20 establishes link 106 with first transceiver 72, and first transceiver 72 transmits to the patient support apparatus the unique identifier 112 corresponding to the headwall unit 76 of that particular bay area 100. The patient support apparatus 20 uses this specific identifier to determine which of the multiple headwall units 76 it is supposed to have second communication link 110 with, and disestablishes any second communication links 110 it may have established with the other headwall unit(s) 76 that do not have the specific identifier it received via communication link 106. The result is that patient support apparatus 20 ends up having a single communication link 110 with one and only one (and the same) headwall unit 76.

Figure 5:
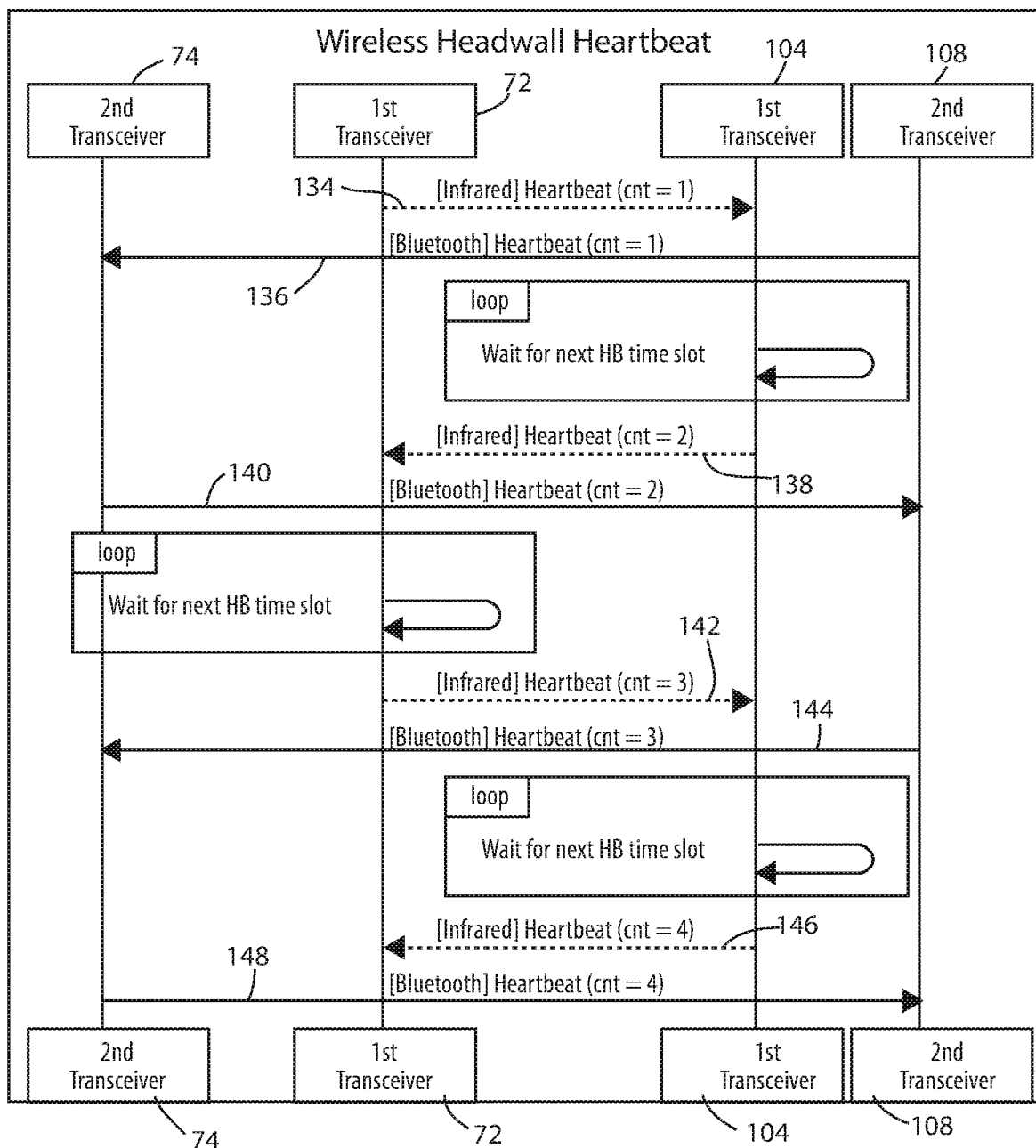
FIG. 5 is a sequence diagram illustrating one manner in which heartbeat messages may be exchanged between the patient support apparatus and the headwall unit.

Once communication links 106 and 110 are established, controllers 92 and 114 maintain the communication links by periodically transmitting heartbeat messages back forth to each other. FIG. 5 illustrates one manner in which controllers 92 and 114 are configured to carry out these heartbeat messages. Controller 92 of headwall unit 76 sends a first heartbeat message at step 134 to patient support apparatus 20 using first transceiver 72. This heartbeat message, as well as the other heartbeat messages discussed herein, includes a counter. First transceiver 104 of patient support apparatus 20 receives this first heartbeat message and passes it to controller 114 of patient support apparatus 20. Instead of acknowledging this heartbeat message using first transceiver 104, controller 114 directs second transceiver 108 to acknowledge this message by sending a return message at step 136. The acknowledgement message is sent off of patient support apparatus 20 via second transceiver 108 and is received at headwall unit 76 by second transceiver 74. The acknowledgement message includes the same counter as the original heartbeat message sent at step 134.

When controller 92 of headwall unit 76 receives this acknowledgement message, it checks the counter and sees that it is the same as the counter it sent at step 134. Because the counter is the same, controller 92 concludes that the first message transmitted via first communication link 106 at step 134 was successfully received. In other words, the successful communication of the first heartbeat message at step 134 over first communication link 106 is acknowledged by a message sent over second communication link 110.

At some moment (the precise time may vary) after acknowledgement of the first heartbeat message is sent at step 136, controller 114 of patient support apparatus 20 sends a second heartbeat message at step 138. Controller 114 uses first transceiver 104 to send this second heartbeat message to first transceiver 72 of headwall unit 76. Controller 114 increments the counter in this message prior to sending it. In response to receiving this second heartbeat message, controller 92 of headwall unit 76 sends an acknowledgement response at step 140. Controller 92 sends the acknowledgement response using second transceiver 74. The acknowledgement message maintains the same counter value that was sent at step 138.

When controller 114 of patient support apparatus 20 receives this second acknowledgement message, it checks the counter and sees that it is the same as the counter it sent at step 138. Because the counter is the same, controller 114 concludes that the second heartbeat message transmitted via first communication link 106 at step 138 was successfully received. In other words, the successful communication of the second heartbeat message at step 138 over first communication link 106 is acknowledged by a second acknowledgement message sent over second communication link 110.

At some point (the precise time may vary) after the acknowledgement message of the second heartbeat message is sent at step 140, controller 92 of headwall unit 76 sends a third heartbeat message at step 142. Controller 92 uses first transceiver 72 of headwall unit 76 to send this third heartbeat message. Controller 92 increments the counter in this heartbeat message prior to sending it. In response to receiving this third heartbeat message, controller 114 of patient support apparatus 20 sends an acknowledgement response at step 144. Controller 114 sends the acknowledgement response using second transceiver 108. The acknowledgement message maintains the same counter value that was sent at step 142.

When controller 92 of headwall unit 76 receives this third acknowledgement message, it checks the counter and sees that it is the same as the counter it sent at step 142. Because the counter is the same, controller 92 concludes that the third heartbeat message transmitted via first communication link 106 at step 142 was successfully received. The successful communication of the third heartbeat message at step 142 over first communication link 106 is therefore acknowledged by a third acknowledgement message sent over second communication link 110.

At some moment (the precise time may vary) after acknowledgement of the third heartbeat message is sent at step 144, controller 114 of patient support apparatus 20 sends a fourth heartbeat message at step 146. Controller 114 uses first transceiver 104 to send this second heartbeat message to first transceiver 72 of headwall unit 76. Controller 114 increments the counter in this message prior to sending it. In response to receiving this fourth heartbeat message, controller 92 of headwall unit 76 sends a fourth acknowledgement response at step 148. Controller 92 sends the fourth acknowledgement response using second transceiver 74. The fourth acknowledgement message maintains the same counter value that was sent at step 146.

When controller 114 of patient support apparatus 20 receives this fourth acknowledgement message, it checks the counter and sees that it is the same as the counter it sent at step 146. Because the counter is the same, controller 114 concludes that the fourth heartbeat message transmitted via first communication link 106 at step 146 was successfully received. The successful communication of the fourth heartbeat message at step 146 over first communication link 106 is acknowledged by the fourth acknowledgement message sent over second communication link 110.

After step 148, controllers 92 and 114 continue to send heartbeat messages back and forth to each other in the manner illustrated in FIG. 5 and just described. As was noted, the time between heartbeat messages and/or acknowledgement messages may be varied. In some embodiments, the time between sending another heartbeat message after sending an acknowledgment message is a fixed and predetermined amount of time. In other embodiments, the time may be variable and/or may be measured from the time the heartbeat message is originally sent. Regardless of the specific manner used to set the frequency of the heartbeat messages and their respective acknowledgements, the period between such messages may vary widely and may be set in order to implement a desired quickness in determining when a communication link failure occurs.

Controllers 92 and 114 may be configured to respond in different manners to the failure to receive an acknowledgement within an expected time period, or the failure of a heartbeat message to be received within an expected time period. In some embodiments, controller 92 and/or 114 issue an alert in response to a single heartbeat message not being received within an expected time period, or in response to a single acknowledgement message not being received within an expected time period. In other embodiments, controllers 92 and/or 114 are configured to wait until more than one expected heartbeat message or acknowledgement is not received before issuing an alert. In still other embodiments, controller 92 and/or 114 may send an inquiry message to the other one in response to a missed expected heartbeat message or acknowledgement. In some embodiments, the inquiry message is sent over the communication link 106, 110 that is not the communication link on which the expected message (heartbeat or acknowledgement) was supposed to be transmitted. For example, if a heartbeat was expected on first communication link 106 but not received, the inquiry message is transmitted over second communication link 110. Still other messages may be passed back and forth between patient support apparatus 20 and headwall unit 76 before either or both of them issue an alert. Such messages may be configured to better diagnose what issue, if any, is present in the communication link(s) 106, 110.

By alternating the heartbeat messages between communication links 106 and 110, the amount of power expended by any given transceiver is reduced. This power saving can be helpful in those situations where headwall unit 76 is battery-operated, and/or where first transceiver 72 is separate from second transceiver 74 and one or both of these transceivers is battery operated.

It will be understood that multiple modifications can be made to the heartbeat messaging illustrated in FIG. 5 and discussed above. For example, although FIG. 5 discloses heartbeat messages that are always sent by one of first transceivers 72, 104 and acknowledgements that are always sent by one of second transceivers 74, 108, this can be reversed. Alternatively, both first transceivers 72, 104 and second transceivers 74, 108 can be used in an alternating fashion to send the heartbeat message with the acknowledgement messages also being alternated. In yet another modified embodiment, the acknowledgement message is sent over the same link 106, 110 as the heartbeat message, but successive heartbeat messages are alternated between the links 106, 110. Still other variations are possible.

In some embodiments, the heartbeat messages are only sent during periods when no other communication is taking place over at least one of the communication links 106, 110 between patient support apparatus 20 and headwall unit 76. In other embodiments, controllers 92 and 114 continue to send heartbeat messages during other communication by interspersing them with the other communication. In still other embodiments, the communication of non-heartbeat messages over links 106, 110 may be carried out by sending acknowledgements of the communicated non-heartbeat messages via the opposite communication link 106, 110 to the link used to communicate the non-heartbeat messages. In other words, in some embodiments, the alternation of communication links 106, 110 is used not just for heartbeat messages, but also for other messages as well.

Figure 6:
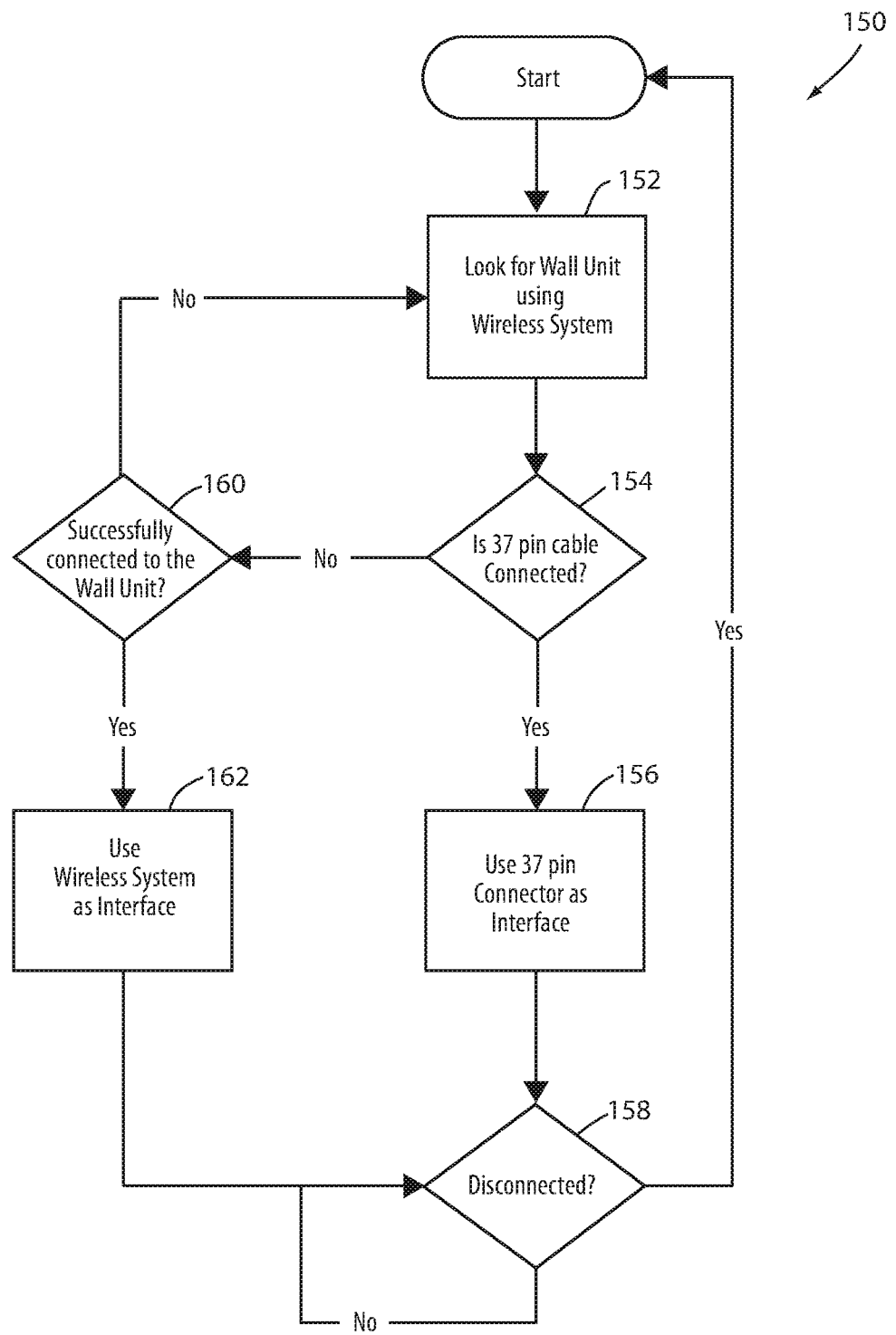
FIG. 6 is a flowchart illustrating a feature of the headwall system in which the patient support apparatus automatically uses a wireless communication link if available and alternatively uses a wired communication link.

FIG. 6 shows a flowchart of a communication selection method 150 according to an embodiment of the present disclosure. Communication method 150 is implemented by controller 114 of patient support apparatus 20. Communication method 150 begins at an initial step 152. At step 152, controller 114 searches for a headwall unit 76 that is within communication range of patient support apparatus 20. In some embodiments, controller 114 accomplishes this by listening to the outputs from transceivers 104, 108 and waiting to detect a beacon signal transmitted from a nearby headwall unit 76. In other embodiments, controller 114 is configured to periodically send out interrogation messages via first and/or second transceivers 104, 108 requesting a response from any headwall unit 76 that is within range of transceivers 104, 108. In still other embodiments, controller 114 accomplishes step 152 through a combination of listening for beacon signals from a headwall unit 76 and sending out interrogation messages to any headwall units 76 within range.

From step 152, controller 114 proceeds to step 154 where it checks to see if a cable 78a (FIG. 4) has been connected between patient support apparatus 20 and cable port 60 of headwall 58. Controller 114 checks for the presence of this cable by using outputs from cable sensor 122 (FIG. 4). If a cable 78a is present, controller 114 proceeds to step 156. At step 156, controller 114 uses the cable 78a to communicate with cable port 60 and its associated components (room interface board 62, nurse call system 64, entertainment devices 66, and/or room lights 68). When using cable 78a in this manner, controller 114 routes all communications to room interface board 62 and its associated components via cable 78a, rather than through a wireless communication link 106, 110. Such cable communication continues until the cable is disconnected at step 158.

If controller 114 does not detect a cable at step 154 (FIG. 6), controller 114 moves to step 160. At step 160, controller 114 checks to see if wireless communication links 106 and 110 have been successfully established between patient support apparatus 20 and a nearby headwall unit 76. If links 106 and 110 have not been established, controller 114 returns to step 152 and proceeds as previously described. If communication links 106, 110 have been established, controller 114 proceeds to step 162 where it uses wireless communication to communicate with room interface board 62 and its associated components. That is, when patient support apparatus 20 communicates data to, for example, nurse call system 64 or entertainment devices 66, controller 114 sends the command via second transceiver 108 (or first transceiver 104, in some cases) to headwall unit 76. Controller 92 of headwall unit 76 receives the data and/or command and forwards it to cable port 60 via cable transceiver 94 and the cable 78 coupled between headwall unit 76 and cable port 60. Cable port 60, as noted, is communicatively coupled to room interface board 62 by a wired connection. Controller 114 continues to use wireless communication at step 162 until the wireless communication links 106, 110 are disestablished at step 158.

Communication method 150 automatically selects wireless communication for communications between patient support apparatus 20 and room interface board 62 (via headwall unit 76) when such wireless communications is available, and automatically selects wired communication if the wireless communication is not available. Communication method 150 prioritizes wireless communication over wired communication because the time it takes for communication links 106, 110 to be established is typically less than the amount of time it takes for a caregiver to plug cable 78a into port 126 and cable port 60. As described previously, this is because communication link 110 is typically automatically established at the time the patient support apparatus 20 enters a room 102 (or sooner, in some case), and communication link 106 is typically automatically established in the moments when patient support apparatus 20 is first moved into a bay area 100. As a result, links 106 and 110 may be established prior to the patient support apparatus 20 stopping movement, and typically before a caregiver has a chance to connect a cable 78a.

It will be appreciated, however, that if a caregiver decides to use a cable 78a for communication after wireless communication links 106, 110 are established, controller 114 will automatically switch to using the cable. This is because cable port 60 typically only includes a single port for a single cable. Thus, if a caregiver couples cable 78a between cable port 60 and patient support apparatus 20 (FIG. 4), the caregiver will typically have to unplug cable 78 between cable port 60 and headwall unit 76. This unplugging is detected by headwall unit 76 and terminates the wireless communication links 106, 110 via step 158 (FIG. 6). Accordingly, method 150 restarts after cable 78 is disconnected from headwall unit 76 and controller 114 detects the presence of cable 78a at step 154. From step 154, controller 114 switches to using cable communications between patient support apparatus 20 and room interface board 62. Method 150 therefore automatically converts to using wired communication if the caregiver plugs cable 78a into patient support apparatus 20, even if wireless communication links 106, 110 were previously established. Similarly, method 150 automatically switches to wireless communication if cable 78a is unplugged and wireless communication links 106, 110 are able to be established.

It will be understood that a number of modifications of method 150 may be implemented. In one such embodiment, controller 114 executes step 160 by looking for at least one communication link 106, 110 and proceeds to step 162 if at least one communication link 106, 110 is established. That is, controller 114 modifies step 162 by proceeding to step 162 after a single communication link 106, 110 is established, rather than waiting for both communication links 106, 110 to be established. At step 162, wireless communication is carried out using whichever communication link 106, 110 is established. Attempts to establish the other communication link 106, 110 continue to be made by controller 114 and, in some embodiments, if success is not achieved with a predetermined time period (or after a predetermined amount of attempts), controller 114 issues an alert. As with all alerts discussed here, the alert may be a local alert (aural and/or visual) on patient support apparatus 20, a remote alert implemented by sending a message via network transceiver 120 to patient support apparatus server 130 and/or alert communication server 128, or a combination of both a local and a remote alert.

In yet another modified embodiment of method 150, headwall unit 76 is modified from the embodiment shown in FIG. 4 and described above. In this modified form, headwall unit 76 includes a pass through cable connector, such as the one connecting cable ports 84a and 84b in FIG. 4 of commonly assigned U.S. patent application Ser. No. 62/600,000, filed Dec. 18, 2017, by inventors Alexander Bodurka., and entitled SMART HOSPITAL HEADWALL SYSTEM, the complete disclosure of which is incorporated herein by reference. Such a pass-through connector allows cable 78a to be connected from patient support apparatus 20 to headwall unit 76, as well as a cable 78 to be connected from headwall unit 76 to cable port 60. With such a pass through connector, cable messages from patient support apparatus 20 to headwall unit 76 are passed therethrough to cable 78, which, as noted, is coupled to headwall port 60.

When headwall unit 76 is modified to include such a cable pass-through connector, patient support apparatus 20 is able to simultaneously communicate with headwall unit 76 via both a wired communication link and one or more wireless communication links. In such embodiments, patient support apparatus 20 can be configured to select whichever communication method is desirable (wired or wireless). In some embodiments, patient support apparatus 20 is configurable by a technician to make whichever choice (wired or wireless) is preferred by an administrator of a healthcare facility. In some of these embodiments, the configuration can be set remotely via server 130 sending a command to the patient support apparatus(es) 20 to implement the preferred communication method. In still other embodiments, headwall unit 76 can be configured to dictate which communication method to choose.

In any of the embodiments where multiple communication links are present, whether wired or wireless, patient support apparatus 20 and headwall unit 76 are configured to automatically switch to using one of the other communication links if there is a failure or malfunction in the link being used. In this manner, the multiple communication links provide redundancy such that the failure of a single communication link does not prevent patient support apparatus 20 from communicating with room interface board 62. In such embodiments, controller 92 and/or controller 114 are configured to issue an alert (local, remote, and/or both) indicating the failure of one or more of the communication links so that appropriate corrective action can be taken. Prior to the corrective action being implemented, communication still continues using whichever link(s) are functional.

Figure 7:
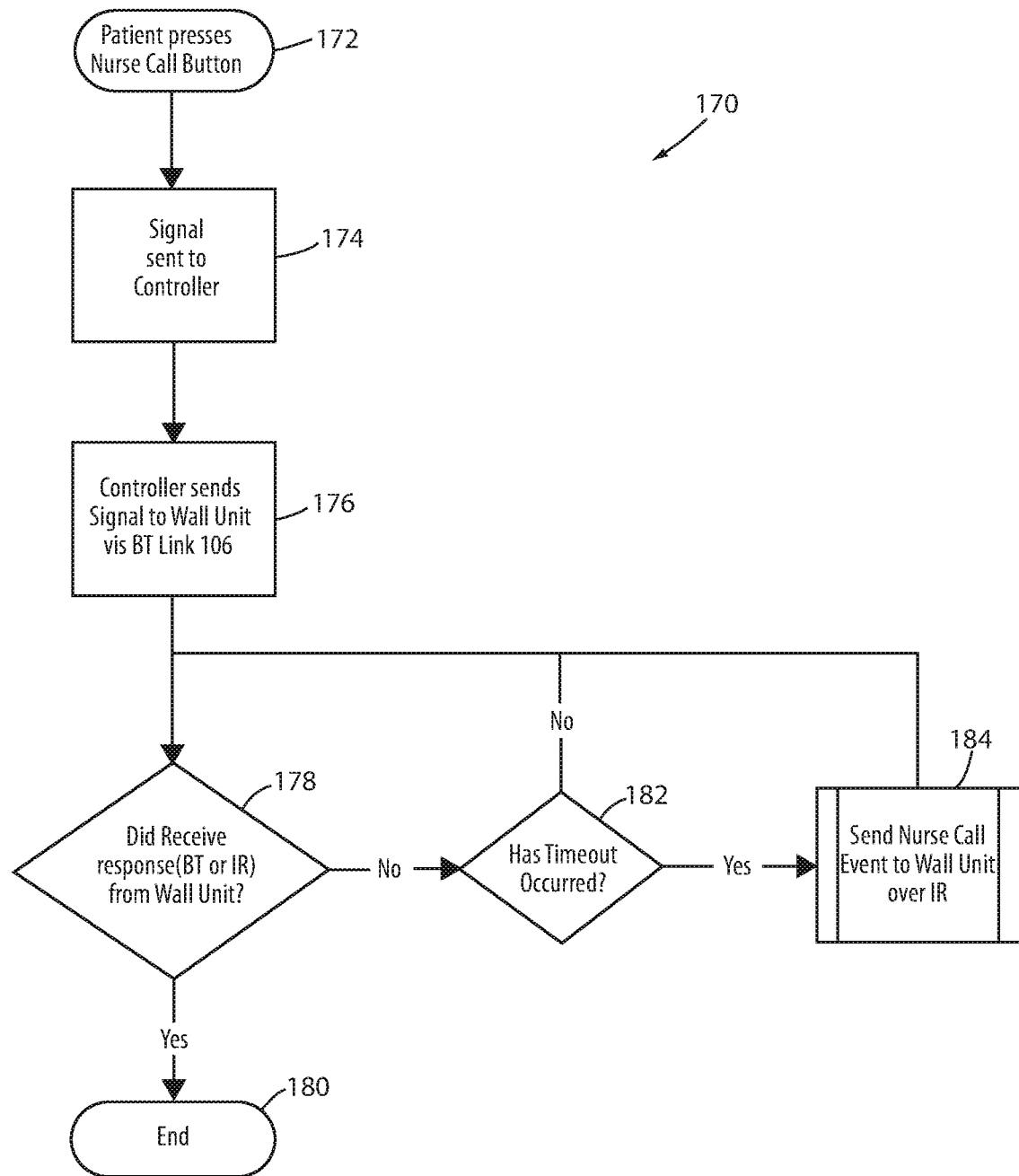
FIG. 7 is flowchart illustrating a feature of the headwall system in which the patient support apparatus automatically switches wireless communication links if a link is inoperative.

FIG. 7 illustrates a communication method 170 implemented by patient support apparatus 20 in at least one embodiment. Communication method 170 utilizes communication links 106, 110 as redundant links and switches to using the other link if a message failure occurs on one of the links 106, 110. Method 170 is implemented by controller 114 and starts at an initial step 172 when a patient presses a nurse call button on patient support apparatus 20, or otherwise activates a nurse call feature on patient support apparatus 20. In many embodiments, the nurse call button (or other activating component) is included within one or both of the patient user interfaces 50c. This nurse call button is activated when the patient wishes to speak with a remotely positioned nurse, or other caregiver.

In response to the nurse call button being pressed at step 172, the button (or other type of device) sends a signal to controller 114 (FIG. 2) at step 174. Controller 114 forwards the signal to headwall unit 76 at step 176 using second transceiver 108. At step 178, controller 114 checks to see if an acknowledgement message indicating the receipt of the signal at step 176 has been received by patient support apparatus 20. The acknowledgement message may be received via first transceiver 104 or second transceiver 108. If such an acknowledgement was received, controller 114 moves to step 180 and method 170 terminates until another nurse call signal or message is to be sent.

If controller 114 does not receive an acknowledgment message back, as determined at step 178, it moves to step 182 and determines whether a timeout period has elapsed yet or not. If the timeout period has not yet elapsed, controller 114 returns to step 178 and checks to see if the acknowledgement message was received yet. Controller 114 thus continues to wait and check for the acknowledgement message until the timeout period of step 182 expires or the acknowledgement is received. If the timeout period expires without an acknowledgement, controller 114 moves to step 184.

At step 184, controller 114 resends the signal sent at step 176 using first transceiver 104. After step 184, controller 114 returns to step 178 to check and see if an acknowledgment of the re-sent signal was received. If it was, controller 114 moves to step 180 and method 170 ends (and restarts when more signals are to be sent). If it was not, controller 114 moves to step 182 to see if the timeout period has expired yet or not. From step 182, controller 114 keeps returning to step 178 until either the acknowledgement of the re-sent signal is received or the timeout period expires. In some embodiments, if the timeout period expires and no acknowledgment of the re-sent signal is received, controller 114 tries to send the signal again using second transceiver 108 and method 170 essentially repeats itself starting at step 176. In other embodiments, after no acknowledgement was received in the timeout period for both the initial signal and the re-sent signal, controller 114 concludes an error exists with respect to both communication links 106 and 110, and issues an alert. The alert may be local, remote, or both.

Although FIG. 7 illustrates method 170 taking place with respect to a signal issued in response to a patient pressing a nurse call button on patient support apparatus 20, it will be understood that method 170 applies to other signals and/or messages sent from patient support apparatus 20 to headwall unit 76. That is, controller 114 uses method 170 when sending any one or more of the following types of messages to headwall unit 76: status messages regarding patient support apparatus 20 (e.g. whether a brake is on or off; whether an exit detection system is armed; whether siderails 34 are raised or lowered; etc.); alerts issued by patient support apparatus 20 (e.g. a patient has exited patient support apparatus 20); commands to one or more devices in communication with room interface board 62 (e.g. a command to turn off a television in the room, a command to change a change a local temperature via thermostat 70, etc.); messages containing audio signals generated by microphone 116 from the patient's voice (which may be packetized); and/or other types of messages.

It will also be understood that method 170 may be modified from the specific embodiment illustrated in FIG. 7 and described herein. For example, in the method shown in FIG. 7, controller 114 first attempts to send a message using second transceiver 108 and second communication link 110. This is done because, in at least one embodiment, second communication link 110 has a higher bandwidth than first communication link 106. However, it will be understood that controller 114 may be programmed to first attempt to use first communication link 106 to send a message and then switch to second communication link 110 if the message is not successfully communicated over first communication link 106. Still further, it will be understood that links 106 and 110, in some embodiments, may be configured to have the same, or substantially the same, bandwidth. Still other modifications to method 170 may be made.

In some embodiments of headwall system 90, communication method 170 is used not only by patient support apparatus 20 when sending message to headwall unit 76, but also by headwall unit 76 when sending messages to patient support apparatus 20. That is, whenever controller 92 of headwall unit 76 sends a message to patient support apparatus 20, it first attempts to send the message using one of communication links 106, 110, and if that fails, it automatically re-sends the message using the other communication link 106, 110. If one or both of the communication links 106, 110 fail, headwall unit 76 may issue a local alert (e.g. via status lights 88 or otherwise), send an alert to nurse call system 64 via room interface board 62, and/or send an alert to headwall server 130 via a network transceiver (not shown) built into headwall unit 76.

Figure 8:
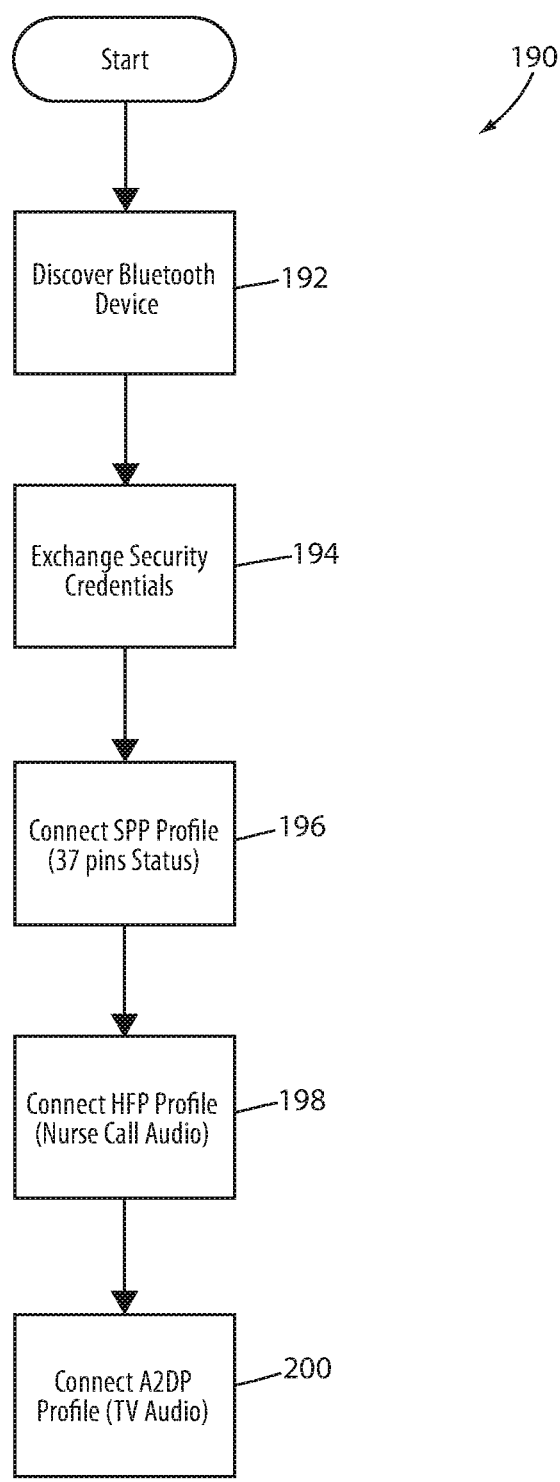
FIG. 8 is flowchart illustrating one manner in which the patient support apparatus may pair with the headwall unit.

FIG. 8 illustrates a connection method 190 utilized in some embodiments by controller 114 of patient support apparatus 20. Controller 114 utilizes method 190 when establishing second communication link 110 that is implemented as a Bluetooth communication link. Method 190 starts at step 192 where second transceivers 74 and 108 discover each other using conventional Bluetooth discovery messages. From step 192, control proceeds to step 194 where second transceivers 74 and 108 exchange their security credentials. This step may be undertaken in a conventional manner using Bluetooth technology, or it may take place in other manners, at least one of which is described in greater detail below with respect to FIG. 9.

After step 194, second transceivers 74 and 108 connect to each other using or more conventional Bluetooth profiles in order to carry out the communication described above. At step 196, transceivers 74 and 108 connect using the Serial Port Profile (SPP). The SPP profile emulates a serial cable and defines how to set up virtual serial ports for transceivers 74 and 108. Patient support apparatus 20 and headwall unit 76, in at least one embodiment, utilize the Serial Port Profile to communicate alerts and messages to nurse call system 64, commands to room interface board 62 (forwarded to entertainment devices 66), and any of the messages not sent using the profiles discussed below with respect to steps 198 and 200.

At step 198, patient support apparatus 20 and headwall unit 76 connect to each other using the conventional Hands Free Profile (HFP) of Bluetooth. Patient support apparatus 20 and headwall unit 76 use this profile to communicate the audio signals for the nurse call communication. That is, the patient's voice signals and the voice signals from the remotely positioned nurse are exchanged between patient support apparatus 20 and headwall unit 76 using the HFP profile and second transceivers 74 and 108.

At step 200, patient support apparatus 20 and headwall unit 76 connect to each other using the Advanced Audio Distribution Profile (A2DP). Headwall unit 76 uses this profile to stream audio signals from entertainment device 66 (e.g. TV, radio, etc.) to patient support apparatus 20. The audio signals are sent to room interface board 62, which forwards them to headwall unit 76 (via cable port 60). Headwall unit 76 transmits them wirelessly to patient support apparatus 20 using A2DP. Controller 114 of patient support apparatus 20 receives the audio signals and directs them to one or more of speakers 54. In this manner, the audio from one or more entertainment devices 66 can be conveyed directly to speakers 54 on patient support apparatus 20.

It will be understood that other conventional profiles may be utilized by headwall unit 76 and patient support apparatus 20 when communicating using a Bluetooth technology (e.g. communication link 110). The assignment of specific protocols to specific types of messages may also be varied from the assignments discussed above. Still further, as has been previously noted, second communication link 110 is implemented in some embodiments using non-Bluetooth technology, in which none of the aforementioned Bluetooth profiles are used.

Figure 9:
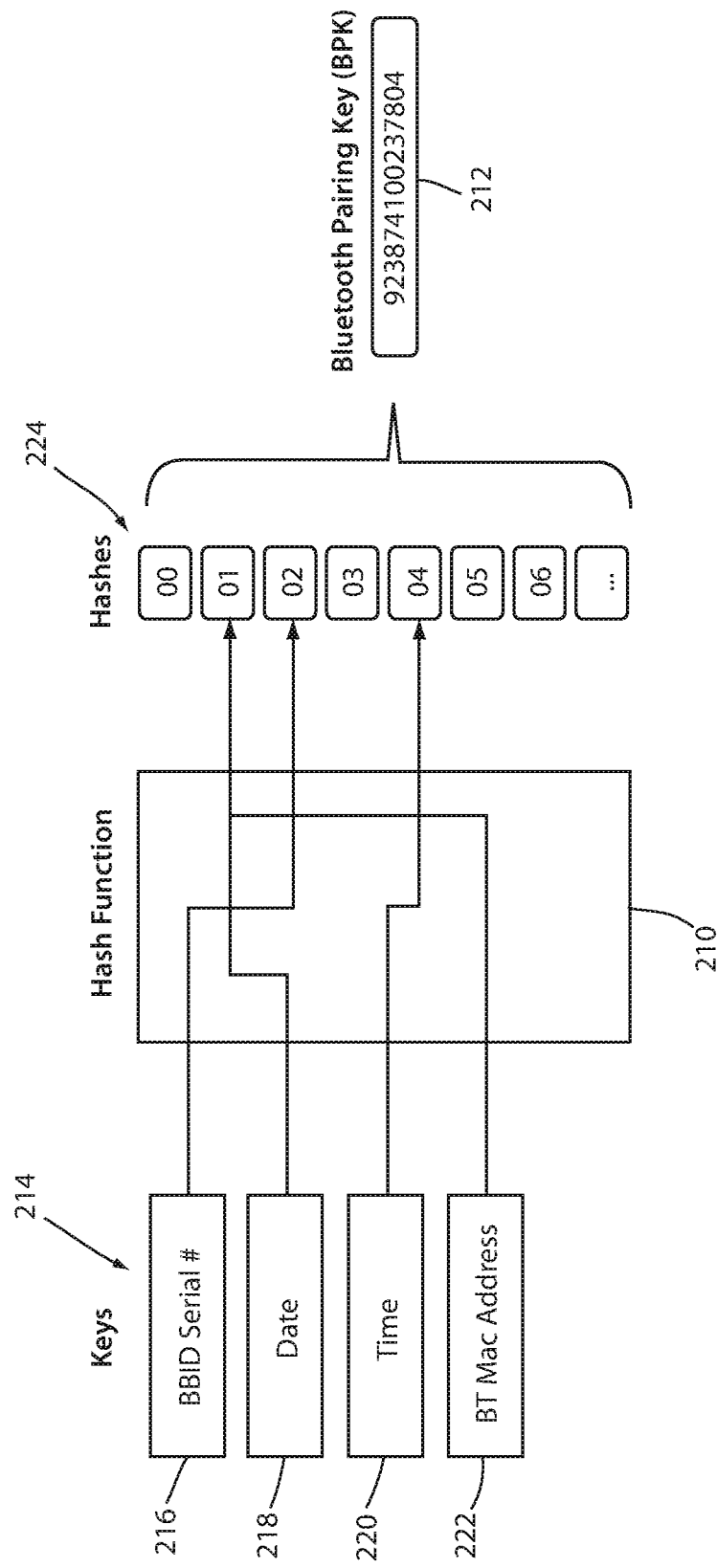
FIG. 9 is a diagram illustrating one manner in which a pairing key may be encoded to improve the security of the communications between the patient support apparatus and the headwall unit.

FIG. 9 illustrates one manner in which security for pairing patient support apparatus 20 with headwall unit 76 may be improved. As with conventional Bluetooth technology, patient support apparatus 20 and headwall unit 76 are able to securely pair to each other when they both possess a shared secret, which is commonly referred to as a link key. The link key is used to authenticate the two devices to each other and to encrypt exchanged data. Patient support apparatuses 20 and headwall units 76 use the link key to prevent non-authorized devices from pairing with either patient support apparatus 20 and/or headwall unit 76, as well as to resist unauthorized devices from decrypting messages exchanged between patient support apparatuses 20 and headwall units 76. Patient support apparatuses 20 and headwall unit 76 are either manufactured with the shared secret (link key), or are configured via authorized personnel to both be in possession of the shared secret (link key).

Patient support apparatus 20 and headwall unit 76 encrypt messages between each other using the link key and a pairing key 212 (FIG. 9). Pairing key 212 is exchanged between the two when the devices are in the process of pairing with each other. In order to prevent unauthorized devices from intercepting pairing key 212 and using it to decrypt the exchanged messages (which would also require knowledge of the link key (shared secret)), pairing key 212 is exchanged between headwall units 76 and patient support apparatus 20 using a hash function 210 known to each device. In some embodiments, such as that illustrated in FIG. 9, hash function 210 is constructed from a plurality of input keys 214, at least some of which are dynamic. That is, at least some of the input keys 214 vary from device to device, and/or vary with respect to other parameters (e.g. time). The dynamic nature of keys 214 betters improves security between patient support apparatuses 20 and headwall units 76. In some embodiments, patient support apparatus 20 and headwall unit 76 may use a location key (not shown) that is based upon the location of headwall unit 76 (e.g. room number, bay area, wing, facility, city, state, etc.).

FIG. 9 illustrates several examples of input keys 214 that may be used by patient support apparatus 20 and headwall unit 76 for inputs into hash function 210. As shown therein, input keys 214 include a serial number 216 for a particular headwall unit 76 (and/or for a particular patient support apparatus 20), a date 218, a time 220, and a Bluetooth Media Access Control (MAC) address 222 for either headwall unit 76 or patient support apparatus 20. It will be understood that this list of input keys 214 is merely illustrative of one specific example of the types of input keys 214 that may be input into hash function 210, and that a large number of other types of input keys 214 may be used.

Whichever set of input keys patient support apparatus 20 and headwall unit 76 are configured to utilize, the input keys 214 are input into hash function 210 to generate a plurality of hashes 224. Hashes 224 are then transmitted to each other. Each recipient (patient support apparatus 20 and headwall unit 76) includes the hash function and utilizes this information and the known keys to determine the pairing key 212. The devices are then able to continue with the pairing process by generating the session key, and to thereafter generate encrypted messages to each other using the pairing key 212 and the link key.

When the pairing key 212 is exchanged between patient support apparatus 20 and headwall unit 76 using hash function 210, both patient support apparatus 20 and headwall unit 76 are configured to exchange the pairing key using out-of-band communication. That is, when pairing key 212 is used to establish second communication link 110 between patient support apparatus 20 and headwall unit 76, pairing key 212 is exchanged between these devices using a different communication link. In some embodiments, patient support apparatus 20 and headwall unit 76 use first communication link 106 to exchange pairing key 212. In other embodiments where headwall unit 76 and patient support apparatus 20 both include network transceivers, pairing key 212 may be exchanged using the network transceivers. Still other communication links may be used. By exchanging pairing key 212 using an out-of-band link, the security of the communication link associated with pairing key 212 (e.g. second communication link 110) is increased.

In order to further improve the security of second communication link 110, pairing key 212 and all session details regarding first and second communication links 106 and 110 are deleted by both patient support apparatus 20 and headwall unit 76 after these communication links are disconnected. In this manner, all keys used for the discovery and connection establishment for both communication links 106, 110, are not saved on either device. This helps to prevent against security attacks because if the keys were somehow intercepted, they could otherwise be re-used to pretend to be an authorized device.

It will be understood that various modifications may be made to the structures and methods of headwall system 90. For example, although headwall unit 76 has been described as being mounted to a headwall 58 of a room 102, it need not be mounted to a wall. Instead, headwall unit 76 can be mounted in any fixed location within a room, including, but not limited to, the ceiling, the floor, or to other architectural structures within the room.

It will also be understood that controller 114 may be modified to communicate with nurse call system 64 via network transceiver 120 in addition to such communication via cable port 60. Communicating via network transceiver 120 can be useful in situations where patient support apparatus 20 has been moved out of a room and is no longer in communication with the headwall unit 76 and/or has been disconnected from cable port 60. By communicating using network transceiver 120, controller 114 is able to send a message to the nurse call system 64 (via access points 96) indicating that it has moved away from headwall unit 76 and/or bay area 100, and the nurse call system 64 can therefore cancel any cord-out alerts that may otherwise have been instituted and/or take other actions knowing that patient support apparatus 20 is no longer positioned at that particular bay area 100.

Still further, it will be understood that headwall unit 76 may interact with patient support apparatus 20 in a wide variety of different manners. As two examples, headwall units 76 and patient support apparatuses 20 may be configured to include any of the components and/or to perform any of the functions described in commonly assigned U.S. patent application Ser. No. 62/600,000 filed Dec. 18, 2017, by inventors Alex Bodurka et al., and entitled SMART HOSPITAL HEADWALL SYSTEM, and/or commonly assigned U.S. provisional patent application Ser. No. 62/587,867 filed Nov. 17, 2017, by inventors Alex Bodurka et al. and entitled PATIENT SUPPORT APPARATUSES WITH LOCATION/MOVEMENT DETECTION, the complete disclosures of both of which are incorporated herein by reference in their entirety.

It will also be understood that the use of the term "transceiver" herein is intended to cover not only devices that include a transmitter and receiver contained within a single unit, but also devices having a transmitter separate from a receiver, and/or any other devices that are capable of both transmitting and receiving signals or messages.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A patient support apparatus comprising:
a support surface adapted to support a patient thereon;
a nurse call control adapted to be activated when the patient wishes to speak to a remotely positioned nurse;
a Bluetooth transceiver adapted to wirelessly communicate with a stationary unit mounted in a room of a healthcare facility;
a wired transceiver adapted to communicate with a nurse call system port mounted to a wall of the room;
an infrared transceiver adapted to wirelessly communicate with the stationary unit; and
a controller adapted to transmit a first signal from the patient support apparatus to the stationary unit in response to the nurse call control being activated, the controller further adapted to initially transmit the first signal to the stationary unit via the Bluetooth transceiver, to wait for a predetermined amount of time to receive an acknowledgement from the stationary unit, and to subsequently transmit the first signal via the infrared transceiver if the controller does not receive the acknowledgement within the predetermined amount of time, the controller further adapted to transmit the first signal from the patient support apparatus to the nurse call system port if the initial attempt to transmit the first signal to the stationary unit using the Bluetooth transceiver and the subsequent attempt to transmit the first signal to the stationary unit using the infrared transceiver are both unsuccessful.

2. The patient support apparatus of claim 1 wherein the controller is adapted to maintain heartbeat messages between the patient support apparatus and the stationary unit while the patient support apparatus is positioned in the room.

3. A patient support apparatus comprising:
a support surface adapted to support a patient thereon;
a nurse call control adapted to be activated when the patient wishes to speak to a remotely positioned nurse;
a Bluetooth transceiver adapted to wirelessly communicate with a stationary unit mounted in a room of a healthcare facility;
a microphone adapted to generate audio signals in response to the patient speaking into the microphone;
an infrared transceiver adapted to wirelessly communicate with the stationary unit; and
a controller adapted to transmit a first signal from the patient support apparatus to the stationary unit in response to the nurse call control being activated, the controller further adapted to initially transmit the first signal to the stationary unit via the Bluetooth transceiver, to wait for a predetermined amount of time to receive an acknowledgement from the stationary unit, and to subsequently transmit the first signal via the infrared transceiver if the controller does not receive the acknowledgement within the predetermined amount of time, and wherein the controller is further adapted to initially transmit the audio signals to the stationary unit via the Bluetooth transceiver, to wait for the predetermined amount of time to receive an audio signal acknowledgement from the stationary unit, and to subsequently transmit the audio signals via the infrared transceiver if the controller does not receive the audio signal acknowledgement within the predetermined amount of time.

4. The patient support apparatus of claim 3 wherein the controller is adapted to only transmit the audio signals via the Bluetooth transceiver after pairing the Bluetooth transceiver with the stationary unit.

5. The patient support apparatus of claim 4 wherein the controller is further adapted to pair the Bluetooth transceiver and the stationary unit by sending a pairing key to the stationary unit via the infrared transceiver.

6. The patient support apparatus of claim 5 wherein the controller is further adapted to delete the pairing key from all memory on the patient support apparatus after a communication session between the Bluetooth transceiver and the stationary unit has ended.

7. The patient support apparatus of claim 6 wherein the controller generates the pairing key using a hash function and a plurality of values.

8. The patient support apparatus of claim 7 wherein the plurality of values includes at least one of the following: a serial number, a Media Access Control (MAC) address, a time, a date, and a location.

9. A patient support apparatus comprising:
a support surface adapted to support a patient thereon;
a nurse call control adapted to be activated when the patient wishes to speak to a remotely positioned nurse;
a Bluetooth transceiver adapted to wirelessly communicate with a stationary unit mounted in a room of a healthcare facility;
an infrared transceiver adapted to wirelessly communicate with the stationary unit; and
a controller adapted to transmit a first signal from the patient support apparatus to the stationary unit in response to the nurse call control being activated, the controller further adapted to initially transmit the first signal to the stationary unit via the Bluetooth transceiver, to wait for a predetermined amount of time to receive an acknowledgement from the stationary unit, and to subsequently transmit the first signal via the infrared transceiver if the controller does not receive the acknowledgement within the predetermined amount of time, and wherein the controller is adapted to maintain heartbeat messages between the patient support apparatus and the stationary unit while the patient support apparatus is positioned in the room.

10. The patient support apparatus of claim 9 wherein the controller is further adapted to alternate the heartbeat messages between the Bluetooth and infrared transceivers.

11. The patient support apparatus of claim 10 wherein each of the heartbeat messages includes a transmission and a heartbeat acknowledgement, and the controller is adapted to respond to a transmission from the stationary unit received via one of the Bluetooth and infrared transceivers with the heartbeat acknowledgement sent over the other of the Bluetooth and infrared transceivers.

12. The patient support apparatus of claim 11 wherein each of the heartbeat messages includes a counter and the controller is adapted to increment the counter after sending the heartbeat acknowledgement.

13. The patient support apparatus of claim 9 wherein the controller is further adapted to issue an alert if the heartbeat messages stop.

14. A patient support apparatus comprising:
a support surface adapted to support a patient thereon;
a sensor adapted to detect a parameter relating to the patient support apparatus;
a Bluetooth transceiver adapted to wirelessly communicate with a stationary unit mounted in a room of a healthcare facility;
a wired transceiver adapted to communicate with a nurse call system port mounted to a wall of the room;
an infrared transceiver adapted to wirelessly communicate with the stationary unit; and
a controller adapted to transmit a first signal from the patient support apparatus to the stationary unit, the first signal containing data regarding the parameter detected by the sensor, the controller further adapted to initially transmit the first signal to the stationary unit via the Bluetooth transceiver, to wait for a predetermined amount of time to receive an acknowledgement from the stationary unit, and to subsequently transmit the first signal via the infrared transceiver if the controller does not receive the acknowledgement within the predetermined amount of time, wherein the controller is further adapted to transmit the first signal from the patient support apparatus to the nurse call system port if the initial attempt to transmit the first signal to the stationary unit using the Bluetooth transceiver and the subsequent attempt to transmit the first signal to the stationary unit using the infrared transceiver are both unsuccessful.

15. The patient support apparatus of claim 14 wherein the controller is adapted to only transmit the first signal via the Bluetooth transceiver after pairing the Bluetooth transceiver and the stationary unit, and wherein the controller is further adapted to pair the Bluetooth transceiver with the stationary unit by sending a pairing key to the stationary unit via the infrared transceiver.

16. The patient support apparatus of claim 15 wherein the controller is further adapted to delete the pairing key from all memory on the patient support apparatus after a communication session between the Bluetooth transceiver and the stationary unit has ended.

17. The patient support apparatus of claim 14 wherein the controller is adapted to maintain heartbeat messages between the patient support apparatus and the stationary unit while the patient support apparatus is positioned in the room.

18. A patient support apparatus comprising:
a support surface adapted to support a patient thereon;
a sensor adapted to detect a parameter relating to the patient support apparatus;
a Bluetooth transceiver adapted to wirelessly communicate with a stationary unit mounted in a room of a healthcare facility;
a microphone adapted to generate audio signals in response to the patient speaking into the microphone;
an infrared transceiver adapted to wirelessly communicate with the stationary unit; and
a controller adapted to transmit a first signal from the patient support apparatus to the stationary unit, the first signal containing data regarding the parameter detected by the sensor, the controller further adapted to initially transmit the first signal to the stationary unit via the Bluetooth transceiver, to wait for a predetermined amount of time to receive an acknowledgement from the stationary unit, and to subsequently transmit the first signal via the infrared transceiver if the controller does not receive the acknowledgement within the predetermined amount of time, and wherein the controller is further adapted to initially transmit the audio signals to the stationary unit via the Bluetooth transceiver, to wait for the predetermined amount of time to receive an audio signal acknowledgement from the stationary unit, and to subsequently transmit the audio signals via the infrared transceiver if the controller does not receive the audio signal acknowledgement within the predetermined amount of time.

19. A patient support apparatus comprising:
a support surface adapted to support a patient thereon;
a sensor adapted to detect a parameter relating to the patient support apparatus, wherein the sensor includes at least one of the following: a brake sensor adapted to detect whether or not a brake has been activated; a height sensor adapted to detect a height of the support surface; a siderail sensor adapted to detect a state of a siderail of the patient support apparatus; an exit detection sensor adapted to detect whether an exit detection system is armed or not; or a scale sensor adapted to detect a weight of the patient;
a Bluetooth transceiver adapted to wirelessly communicate with a stationary unit mounted in a room of a healthcare facility;
an infrared transceiver adapted to wirelessly communicate with the stationary unit; and
a controller adapted to transmit a first signal from the patient support apparatus to the stationary unit, the first signal containing data regarding the parameter detected by the sensor, the controller further adapted to initially transmit the first signal to the stationary unit via the Bluetooth transceiver, to wait for a predetermined amount of time to receive an acknowledgement from the stationary unit, and to subsequently transmit the first signal via the infrared transceiver if the controller does not receive the acknowledgement within the predetermined amount of time.

20. A patient support apparatus comprising:
a support surface adapted to support a patient thereon;
a sensor adapted to detect a parameter relating to the patient support apparatus;
a Bluetooth transceiver adapted to wirelessly communicate with a stationary unit mounted in a room of a healthcare facility;
an infrared transceiver adapted to wirelessly communicate with the stationary unit; and
a controller adapted to transmit a first signal from the patient support apparatus to the stationary unit, the first signal containing data regarding the parameter detected by the sensor, the controller further adapted to initially transmit the first signal to the stationary unit via the Bluetooth transceiver, to wait for a predetermined amount of time to receive an acknowledgement from the stationary unit, and to subsequently transmit the first signal via the infrared transceiver if the controller does not receive the acknowledgement within the predetermined amount of time, and wherein the controller is adapted to maintain heartbeat messages between the patient support apparatus and the stationary unit while the patient support apparatus is positioned in the room, and wherein the controller is further adapted to alternate the heartbeat messages between the Bluetooth and infrared transceivers.

* * * * *